United States Patent
Ackermann et al.

(10) Patent No.: US 7,495,001 B2
(45) Date of Patent: Feb. 24, 2009

(54) BENZANNELATED DERIVATIVES, THEIR MANUFACTURE AND USE AS PHARMACEUTICAL AGENTS

(75) Inventors: Jean Ackermann, Riehen (CH); Johannes Aebi, Basel (CH); Alfred Binggeli, Binningen (CH); Uwe Grether, Loerrach (DE); Georges Hirth, Colmar (FR); Bernd Kuhn, Liestal (CH); Hans-Peter Maerki, Basel (CH); Markus Meyer, Nuenburg (DE); Peter Mohr, Basel (CH); Matthew Blake Wright, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 630 days.

(21) Appl. No.: 10/977,651

(22) Filed: Oct. 29, 2004

(65) Prior Publication Data
US 2005/0096336 A1    May 5, 2005

(30) Foreign Application Priority Data
Nov. 5, 2003    (EP) .................................. 03104082

(51) Int. Cl.
| A01N 43/54 | (2006.01) |
| A61K 31/435 | (2006.01) |
| C07D 239/02 | (2006.01) |
| C07D 211/70 | (2006.01) |

(52) U.S. Cl. ....................... 514/256; 514/277; 514/357; 544/335; 546/335

(58) Field of Classification Search ................ 546/335, 546/334; 514/277, 357, 256; 544/335
See application file for complete search history.

(56) References Cited

FOREIGN PATENT DOCUMENTS

| EP | 1 266 888 A1 | 12/2002 |
| WO | WO 97/27858 A1 | 8/1997 |
| WO | WO 02/08188 A1 | 1/2002 |
| WO | WO 02/092084 | 11/2002 |
| WO | WO 03/072100 A1 | 9/2003 |
| WO | WO 03/084916 A2 | 10/2003 |
| WO | WO 03084916 | * 10/2003 |

OTHER PUBLICATIONS

2003:818386 HCAPLUS, WO 2003084916 A2 Oct. 16, 2003, Filzen et al.*
Anal. Biochem. 257: 112-119.
Belostotskii, Anatoly M., et. al., Tetrahedron Lett (1994), 35(28), 5075-6.
E.J. Corey, et. al., Am. Chem. Soc (1987) 109, 5551-5553.
Guerre-Millo, et. al., J. Biol Chem (2000) 275: 16638-16642.
Lobiner, et. al., Tetrahedron Lett. (1984), 25, 2535-3536.
S.W. McCombie, et. al., Bioorganic & Medicinal Chemistry Ltrs 13 (2003) 567-571.
Oliver, et. al., Proc Nat Acad Sci USA (2001) 98: 5306-11.
P.V. Ramachandran, e.t al., Tetrahedron: Asymmetry (1994) 5, 1061-1074.
Tetrahedron Letters 43 (42), 7617-7619 (2002).
J. Labelled Compounds & Radiopharmaceuticals 43 (7), 683-691 (2000).
P. Keller, Bull. Soc. Fr. (1994) 131, 27-29.
W. Zhi-Liang, et. al., J. Org. Chem. (2003)web publication release Oct. 10, 2003.
Patent Abstracts of Japan, vol. 2003, No. 10, (2003) & JP 2003 171275 A (Sumitomo Pharmaceut Co Ltd), (2003) Abstract.
Patent Abstracts of Japan, vol. 2003, No. 12, (2003) & JP 2003 292439 A (Sumitomo Pharmaceut Co Ltd), (2003) Abstract.

* cited by examiner

*Primary Examiner*—Janet L Andres
*Assistant Examiner*—Binta M Robinson
(74) *Attorney, Agent, or Firm*—George W. Johnston; Patricia S. Rocha-Tramaloni

(57) ABSTRACT

There are presented compounds of the formula

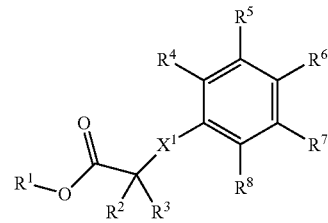

wherein $R^6$ and $R^7$ is

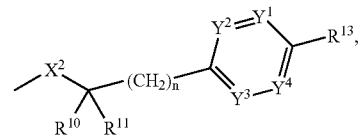

$R^4$ and $R^5$ or $R^5$ and $R^6$ together with the carbon atoms to which they are attached, form a ring as defined in the description and $X^1$, $X^2$, $Y^1$ to $Y^4$, $R^1$ to $R^{13}$ and n are as specified in the description, and to all enantiomers and pharmaceutically acceptable salts and/or esters thereof. The invention further relates to pharmaceutical compositions containing such compounds, to a process for their preparation and to their use for the treatment and/or prevention of diseases which are modulated by PPARδ and/or PPARα agonists.

22 Claims, No Drawings

BENZANNELATED DERIVATIVES, THEIR MANUFACTURE AND USE AS PHARMACEUTICAL AGENTS

SUMMARY OF THE INVENTION

The present invention is concerned with novel benzannelated compounds of the formula

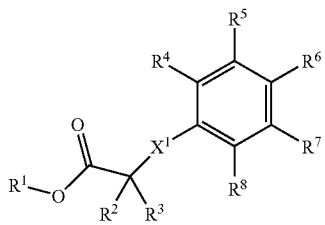

I and enantiomers and pharmaceutically acceptable salts and esters thereof, wherein $X^1$ and $R^{1-8}$ are as described herein.

Chromanyl and indanyl derivatives are described in PCT patent application WO 03/084916.

Compounds of formula I are useful as lipid modulators and insulin sensitizers. In particular, compounds of formula I are PPAR activators.

BACKGROUND OF THE INVENTION

Peroxisome Proliferator Activated Receptors (PPARs) are members of the nuclear hormone receptor superfamily. The PPARs are ligand-activated transcription factors that regulate gene expression and control multiple metabolic pathways. Three subtypes have been described which are PPARα, PPARδ (also known as PPARβ), and PPARγ. PPARδ is ubiquitously expressed. PPARα is predominantly expressed in the liver, kidney and heart. There are at least two major isoforms of PPARγ. PPARγ1 is expressed in most tissues, and the longer isoform, PPARγ2 is almost exclusively expressed in adipose tissue. The PPARs modulate a variety of physiological responses including regulation of glucose- and lipid-homeostasis and metabolism, energy balance, cell differentiation, inflammation and cardiovascular events.

Approximately half of all patients with coronary artery disease have low concentrations of plasma HDL cholesterol. The atheroprotective function of HDL was first highlighted almost 25 years ago and stimulated exploration of the genetic and environmental factors that influence HDL levels. The protective function of HDL comes from its role in a process termed reverse cholesterol transport. HDL mediates the removal of cholesterol from cells in peripheral tissues including those in the atherosclerotic lesions of the arterial wall. HDL then delivers its cholesterol to the liver and sterol-metabolizing organs for conversion to bile and elimination. Data from the Framingham study showed that HDL-C levels are predictive of coronary artery disease risk independently of LDL-C levels. The estimated age-adjusted prevalence among Americans age 20 and older who have HDL-C of less than 35 mg/dl is 16% (males) and 5.7% (females). A substantial increase of HDL-C is currently achieved by treatment with niacin in various formulations. However, the substantial side-effects limit the therapeutic potential of this approach.

As many as 90% of the 14 million diagnosed type 2 diabetic patients in the US are overweight or obese, and a high proportion of type 2 diabetic patients have abnormal concentrations of lipoproteins. The prevalence of total cholesterol >240 mg/dl is 37% in diabetic men and 44% in women. The respective rates for LDL-C>160 mg/dl are 31% and 44%, respectively, and for HDL-C<35 mg/dl 28% and 11%, respectively. Diabetes is a disease in which a patient's ability to control glucose levels in blood is decreased because of partial impairment in response to the action of insulin. Type II diabetes (T2 D) is also called non-insulin dependent diabetes mellitus (NIDDM) and afflicts 80-90% of all diabetic patients in developed countries. In T2 D, the pancreatic Islets of Langerhans continue to produce insulin. However, the target organs for insulin action, mainly muscle, liver and adipose tissue, exhibit a profound resistance to insulin stimulation. The body continues to compensate by producing unphysiologically high levels of insulin, which ultimately decreases in later stage of disease, due to exhaustion and failure of pancreatic insulin-producing capacity. Thus T2 D is a cardiovascular-metabolic syndrome associated with multiple comorbidities including insulin resistance, dyslipidemia, hypertension, endothelial dysfunction and inflammatory atherosclerosis.

First line treatment for dyslipidemia and diabetes generally involves a low-fat and low-glucose diet, exercise and weight loss. However, compliance can be moderate, and as the disease progresses, treatment of the various metabolic deficiencies becomes necessary with e.g. lipid-modulating agents such as statins and fibrates for dyslipidemia and hypoglycemic drugs, e.g. sulfonylureas or metformin for insulin resistance. A promising new class of drugs has recently been introduced that resensitizes patients to their own insulin (insulin sensitizers), thereby restoring blood glucose and triglyceride levels to normal, and in many cases, obviating or reducing the requirement for exogenous insulin. Pioglitazone (ActoS™) and rosiglitazone (Avandia™) belong to the thiazolidinedione (TZD) class of PPARγ-agonists and were the first in their class to be approved for NIDDM in several countries. These compounds, however, suffer from side effects, including rare but severe liver toxicity (as seen with troglitazone). They also increase body weight in patients. Therefore, new, more efficacious drugs with greater safety and lower side effects are urgently needed. Recent studies provide evidence that agonism of PPARδ would result in compounds with enhanced therapeutic potential, i.e. such compounds should improve the lipid profile, with a superior effect on HDL-C raising compared to current treatments and with additional positive effects on normalization of insulin-levels (Oliver et al; Proc Nat Acad Sci USA 2001; 98: 5306-11). Recent observations also suggest that there is a independent PPARα mediated effect on insulin-sensitzation in addition to its well known role in reducing triglycerides (Guerre-Millo et al; J Biol Chem 2000; 275: 16638-16642). Thus selective PPARδ agonists or PPARδ agonists with additional PPARα activity may show superior therapeutic efficacy without the side-effects such as the weight gain seen with PPARγ agonists.

The novel compounds of the present invention exceed the compounds known in the art, inasmuch as they bind to and selectively activate PPARδ or coactivate PPARδ and PPARα simultaneously and very efficiently, and with much improved pharmacokinetic properties. Therefore, these compounds combine the anti-dyslipidemic and anti-glycemic effects of PPARδ and PPARα activation with no effect on PPARγ. Consequently, HDL cholesterol is increased, triglycerides lowered (=improved lipid profile) and plasma glucose and insulin are reduced (=insulin sensitization). In addition, such compounds may also lower LDL cholesterol, decrease blood pressure and counteract inflammatory atherosclerosis. Furthermore, such compounds may also be useful for treating inflammatory diseases such as rheumatoid arthritis, osteoarthritis, and psoriasis. Since multiple facets of combined dyslipidemia and the T2 D disease syndrome are addressed by PPARδ selective agonists and PPARδ and α coagonists, they are expected to have an enhanced therapeutic potential compared to the compounds already known in the art.

Object of the present invention therefore is to provide compounds which must have the criteria mentioned above. Furthermore, the compounds of the present invention exhibit improved pharmacological properties compared to known compounds.

DETAILED DESCRIPTION OF THE INVENTION

The present invention is concerned with novel benzannelated compounds of the formula

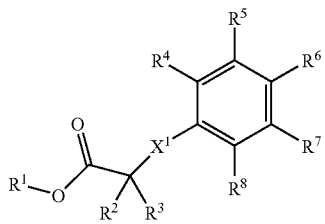

I and enantiomers and pharmaceutically acceptable salts and esters thereof, wherein $X^1$ is O, S, or $CH_2$;
$R^1$ is hydrogen or $C_{1-7}$-alkyl;
$R^2$ is hydrogen or $C_{1-7}$-alkyl,
  or, if $X^1$ is $CH_2$, $R^2$ is hydrogen, $C_{1-7}$-aklyl or $C_{1-7}$-alkoxy;
$R^3$ is hydrogen or $C_{1-7}$-alkyl;
$R^4$ and $R^5$ or $R^5$ and $R^6$ are bonded to each other to form a ring together with the carbon atoms to which they are attached, and $R^4$ and $R^5$ or $R^5$ and $R^6$ together are:
  —CH=CH—CH=CH—,
  —CH=CH—S—, —S—CH=CH—, —CH=CH—O—, —O—CH=CH—,
  —$(CH_2)_p$—, —O—$(CH_2)_q$— or —$(CH_2)_q$—O—,
  wherein p is 3, 4 or 5 and q is 2 or 3; and

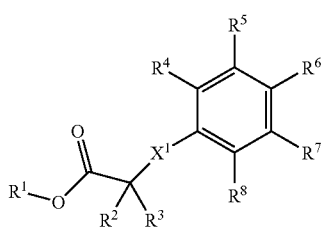

I $R^4$ and $R^6$ are engaged in a ring structure as defined above or independently from each other are selected from the group selected from consisting of hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, cyano-$C_{1-7}$-alkyl or cyano;

$R^7$ and $R^8$ independently from each other are selected from the group consisting of hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, cyano-$C_{1-7}$-alkyl or cyano;

and one of $R^6$ and $R^7$ is

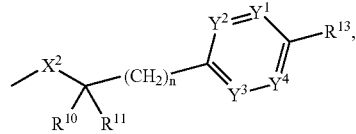

wherein
$X^2$ is S, O, or $NR^9$;
$R^9$ is hydrogen, $C_{1-7}$-alkyl, $C_{3-7}$-cycloalkyl, fluoro-$C_{1-7}$-alkyl, hydroxy-$C_{2-7}$-alkyl, or $C_{1-7}$-alkoxy-$C_{2-7}$-alkyl;
$Y^1, Y^2, Y^3$ and $Y^4$ are N or C—$R^{12}$, and 1 or 2 of $Y^1, Y^2, Y^3$ and $Y^4$ are N and the other ones are C—$R^{12}$;
$R^{10}$ is hydrogen, $C_{1-7}$-alkyl, $C_{3-7}$-cycloalkyl, or fluoro-$C_{1-7}$-alkyl;
$R^{11}$ is hydrogen, $C_{1-7}$-alkyl, or $C_{1-7}$-alkoxy-$C_{1-7}$-alkyl;
$R^{12}$ independently from each other in each occurrence is selected from the group consisting of hydrogen, $C_{1-7}$-alkyl, $C_{3-7}$-cycloalkyl, fluoro-$C_{1-7}$-alkyl, $C_{1-7}$-alkoxy-$C_{1-7}$-alkyl, hydroxy-$C_{1-7}$-alkyl, $C_{1-7}$-alkylthio-$C_{1-7}$-alkyl, carboxy-$C_{1-7}$-alkoxy-$C_{1-7}$-alkyl, carboxy-$C_{1-7}$-alkyl, mono- or di-$C_{1-7}$-alkyl-amino-$C_{1-7}$-alkyl, $C_{1-7}$-alkanoyl-$C_{1-7}$-alkyl, $C_{2-7}$-alkenyl, and $C_{2-7}$-alkinyl;
$R^{13}$ is aryl or heteroaryl; and
n is 0, 1 or 2;

provided that compounds of formula I are excluded, wherein $X^1$ is O, $R^2$ and $R^3$ are hydrogen,
$R^6$ is equal to

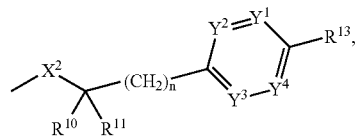

$X^2$ is O or S, and $R^{10}$ and $R^{11}$ are hydrogen.

Unless otherwise indicated the following definitions are set forth to illustrate and define the meaning and scope of the various terms used to describe the invention herein.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl" or "$C_{1-7}$-alkyl", alone or in combination with other groups, refers to a branched or straight-chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the groups specifically exemplified herein.

The term "halogen" refers to fluorine, chlorine, bromine and iodine.

The term "fluoro-lower alkyl" or "fluoro-$C_{1-7}$-alkyl" refers to to lower alkyl groups which are mono- or multiply substituted with fluorine. Examples of fluoro-lower alkyl groups are e.g. —$CF_3$, —$CH_2CF_3$, —$CH(CF_3)_2$ and the groups specifically exemplified herein.

The term "alkoxy" refers to the group R'—O—, wherein R' is alkyl. The term "lower-alkoxy" or "$C_{1-7}$-alkoxy" refers to the group R'—O—, wherein R' is lower-alkyl. Examples of lower-alkoxy groups are e.g. methoxy, ethoxy, prop oxy, isopropoxy, butoxy, isobutoxy and hexyloxy. Preferred are the lower-alkoxy groups specifically exemplified herein.

The term "alkylthio" refers to the group R'—S—, wherein R' is alkyl. The term "lower-alkylthio" or "$C_{1-7}$-alkylthio" refers to the group R'—S—, wherein R' is lower-alkyl. Examples of $C_{1-7}$-alkylthio groups are e.g. methylthio or ethylthio. Preferred are the lower-alkylthio groups specifically exemplified herein.

The term "mono- or di-$C_{1-7}$-alkyl-amino" refers to an amino group, which is mono- or disubstituted with $C_{1-7}$-alkyl. A mono-$C_{1-7}$-alkyl-amino group includes for example methylamino or ethylamino. The term "di-$C_{1-7}$-alkyl-amino" includes for example dimethylamino, diethylamino or ethylmethylamino. Preferred are the mono- or di-$C_{1-7}$-alkylamino groups specifically exemplified herein.

The term "carboxy-lower alkyl" or "carboxy-$C_{1-7}$-alkyl" refers to to lower alkyl groups which are mono- or multiply substituted with a carboxy group (—COOH). Examples of carboxy-lower alkyl groups are e.g. —$CH_2$—COOH (carboxymethyl), —$(CH_2)_2$—COOH (carboxyethyl) and the groups specifically exemplified herein.

The term "alkanoyl" refers to the group R'—CO—, wherein R' is alkyl. The term "lower-alkanoyl" or "$C_{1-7}$-alkanoyl" refers to the group R'—O—, wherein R' is lower-alkyl. Examples of lower-alkanoyl groups are e.g. ethanoyl (acetyl) or propionyl. Preferred are the lower-alkoxy groups specifically exemplified herein.

The term "lower alkenyl" or "$C_{2-7}$-alkenyl", alone or in combination, signifies a straight-chain or branched hydrocarbon residue comprising an olefinic bond and up to 7, preferably up to 6, particularly preferred up to 4 carbon atoms. Examples of alkenyl groups are ethenyl, 1-propenyl, 2-propenyl, isopropenyl, 1-butenyl, 2-butenyl, 3-butenyl and isobutenyl. A preferred example is 2-propenyl.

The term "lower alkinyl" or "$C_{2-7}$-alkinyl", alone or in combination, signifies a straight-chain or branched hydrocarbon residue comprising a triple bond and up to 7, preferably up to 6, particularly preferred up to 4 carbon atoms. Examples of alkinyl groups are ethinyl, 1-propinyl, or 2-propinyl.

The term "cycloalkyl" or "$C_{3-7}$-cycloalkyl" denotes a saturated carbocyclic group containing from 3 to 7 carbon atoms, such as cyclopropyl, cyclobutyl, cyclopentyl, cyclohexyl or cycloheptyl.

The term "aryl" relates to the phenyl or naphthyl group, preferably the phenyl group, which can optionally be mono- or multiply-substituted, particularly mono- or di-substituted by halogen, hydroxy, CN, $CF_3$, $NO_2$, $NH_2$, N(H, lower-alkyl), N(lower-alkyl)$_2$, carboxy, aminocarbonyl, lower-alkyl, lower fluoroalkyl, lower-alkoxy, lower fluoroalkoxy, aryl and/or aryloxy. Preferred substituents are halogen, $CF_3$, lower-alkyl, lower fluoroalkoxy and/or lower-alkoxy. Preferred are the specifically exemplified aryl groups.

The term "heteroaryl" refers to an aromatic 5- or 6-membered ring which can comprise 1, 2 or 3 atoms selected from nitrogen, oxygen and/or sulphur such as furyl, pyridyl, 1,2-, 1,3- and 1,4-diazinyl, thienyl, isoxazolyl, oxazolyl, imidazolyl, or pyrrolyl. The term "heteroaryl" further refers to bicyclic aromatic groups comprising two 5- or 6-membered rings, in which one or both rings can contain 1, 2 or 3 atoms selected from nitrogen, oxygen or sulphur such as e.g. indole or quinoline, or partially hydrogenated bicyclic aromatic groups such as e.g. indolinyl. A heteroaryl group may have a substitution pattern as described earlier in connection with the term "aryl". Preferred heteroaryl groups are e.g. thienyl and furyl which can optionally be substituted as described above, preferably with halogen, $CF_3$, lower-alkyl and/or lower-alkoxy.

The term "protecting group" refers to groups such as e.g. acyl, alkoxycarbonyl, aryloxycarbonyl, benzyl, silyl, or imine-derivatives, which are used to temporarily block the reactivity of functional groups. Well known protecting groups are e.g. t-butyloxycarbonyl, benzyloxycarbonyl, fluorenylmethyloxycarbonyl or diphenylmethylene which can be used for the protection of amino groups, or lower-alkyl-, β-trimethylsilylethyl- and β-trichloroethyl-esters, which can be used for the protection of carboxy groups. Protecting groups which can be used for the protection of hydroxy groups are e.g. benzyl, trimethylsilyl or tert-butyldimethylsilyl.

"Isomers" are compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a ("chiral center".

The term "pharmaceutically acceptable salts" embraces salts of the compounds of formula (I) with pharmaceutically acceptable bases such as alkali salts, e.g. Na- and K-salts, alkaline earth salts, e.g. Ca- and Mg-salts, and ammonium or substituted ammonium salts, such as e.g. trimethylammonium salts. The term "pharmaceutically acceptable salts" also relates to such salts.

The compounds of formula (I) can also be solvated, e.g. hydrated. The solvation can be effected in the course of the manufacturing process or can take place e.g. as a consequence of hygroscopic properties of an initially anhydrous compound of formula (I) (hydration). The term pharmaceutically acceptable salts also includes pharmaceutically acceptable solvates.

The term "pharmaceutically acceptable esters" embraces derivatives of the compounds of formula (I), in which a carboxy group has been converted to an ester. Lower-alkyl, hydroxy-lower-alkyl, lower-alkoxy-lower-alkyl, amino-lower-alkyl, mono- or di-lower-alkyl-amino-lower-alkyl, morpholino-lower-alkyl, pyrrolidino-lower-alkyl, piperidino-lower-alkyl, piperazino-lower-alkyl, lower-alkyl-piperazino-lower-alkyl and aralkyl esters are examples of suitable esters. The methyl, ethyl, propyl, butyl and benzyl esters are preferred esters. The methyl and ethyl esters are especially preferred. The term "pharmaceutically acceptable esters" furthermore embraces compounds of formula (I) in which hydroxy groups have been converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

Preferred compounds of formula I of the present invention are compounds, wherein $R^1$ is hydrogen.

Also preferred are compounds of formula I of the present invention, wherein $X^2$ is —$NR^9$ and $R^9$ is hydrogen, $C_{1-7}$-alkyl, $C_{3-7}$-cycloalkyl, fluoro-$C_{1-7}$-alkyl, hydroxy-$C_{2-7}$-alkyl, or $C_{1-7}$-alkoxy-$C_{2-7}$-alkyl.

Especially preferred are those compounds of formula I, wherein $R^9$ is $C_{1-7}$-alkyl. More preferably, $R^9$ is methyl.

Examples of such preferred compounds are the following:

[rac]-[4-(methyl-{1-[2-methyl-6-(4-trifluoromethyl-phenyl)-pyridin-3-yl]-ethyl}-amino)-naphthalen-1-yloxy]-acetic acid;

[rac]-[4-(methyl-{1-[2-methyl-6-(3-trifluoromethyl-phenyl)-pyridin-3-yl]-propyl}-amino)-naphthalen-1-yloxy]-acetic acid;

[rac]-[4-(methyl-{1-[2-methyl-6-(3-trifluoromethyl-phenyl)-pyridin-3-yl]-butyl}-amino)-naphthalen-1-yloxy)-acetic acid, and 2-methyl-2-(4-{methyl-[2-methyl-6-(4-trifluoromethyl-phenyl)-pyridin-3-ylmethyl]-amino}-5,6,7,8-tetrahydro-naphthalen-1-yloxy)-propionic acid.

Furthermore, compounds of formula I in accordance with the present invention are preferred, wherein $X^1$ is S or $CH_2$.

Especially preferred are compounds of formula I, wherein $X^1$ is $CH_2$.

The following compounds are examples for such compounds:

[rac]-2-methoxy-3-(4-{2-[2-methyl-6-(4-trifluoromethyl-phenyl)-pyridin-3-yl]-ethoxy}-naphthalen-2-yl)-propionic acid;

3-{4-[2-methyl-6-(4-trifluoromethyl-phenyl)-pyridin-3-ylmethoxy]-5,6,7,8-tetrahydro-naphthalen-1-yl}-propionic acid; and 3-{4-[2-methyl-6-(4-trifluoromethyl-phenyl)-pyridin-3-ylmethoxy]-naphthalen-1-yl}-propionic acid.

Further examples of such compounds are:

3-(4-{2-[2-methyl-6-(4-trifluoromethyl-phenyl)-pyridin-3-yl]-ethoxy}-5,6,7,8-tetrahydro-naphthalen-1-yl)-propionic acid, 3-(4-{2-[2-methyl-6-(4-trifluoromethyl-phenyl)-pyridin-3-yl]-ethoxy}-naphthalen-1-yl)-propionic acid, 3-{4-[4-cyclopropyl-2-(4-trifluoromethyl-phenyl)-pyrimidin-5-ylmethoxy]-naphthalen-1-yl}-propionic acid, 3-{4-[4-cyclopropyl-2-(4-trifluoromethyl-phenyl)-pyrimidin-5-ylmethoxy]-5,6,7,8-tetrahydro-naphthalen-1-yl}-propionic acid, and 3-{4-[5-(4-trifluoromethyl-phenyl)-pyrimidin-2-ylmethoxy]-naphthalen-1-yl}-propionic acid.

Preferred compounds of formula I of the present invention are those, wherein $R^4$ and $R^5$ or $R^5$ and $R^6$ are bonded to each other to form a ring together with the carbon atoms to which they are attached, and $R^4$ and $R^5$ or $R^5$ and $R^6$ together are —CH=CH—CH=CH— or —$(CH_2)_p$— with p being 4. Especially preferred are those compounds wherein $R^4$ and $R^5$ or $R^5$ and $R^6$ together are —CH=CH—CH=CH—.

Further preferred compounds of formula I are those, wherein $R^{10}$ is $C_{1-7}$-alkyl. More preferably, $R^{10}$ is methyl or ethyl.

An example of such a compound is [rac]-(4-{1-[2-methyl-6-(4-trifluoromethyl-phenyl)-pyridin-3-yl]-ethoxy}-naphthalen-1-yloxy)-acetic acid.

Also preferred are compounds of formula I according to the present invention, wherein $R^2$ is $C_{1-7}$-alkyl. More preferably, $R^2$ is methyl.

Especially preferred are compounds of formula I are those, wherein $R^2$ and $R^3$ are $C_{1-7}$-alkyl. More preferably, $R^2$ and $R^3$ are methyl.

Furthermore, preferred compounds of formula I of the present invention are those, wherein $X^1$ is O and $R^2$ and $R^3$ are $C_{1-7}$-alkyl.

The following compounds are preferred examples thereof:

2-methyl-2-(3-{2-[2-methyl-6-(4-trifluoromethyl-phenyl)-pyridin-3-yl]-ethoxy}-naphthalen-1-yloxy)-propionic acid, 2-methyl-2-{3-[2-methyl-6-(4-trifluoromethyl-phenyl)-pyridin-3-ylmethoxy]-naphthalen-1-yloxy}-propionic acid, 2-(3-{2-[4-cyclopropyl-2-(4-trifluoromethyl-phenyl)-pyrimidin-5-yl]-ethoxy}-naphthalen-1-yloxy)-2-methyl-propionic acid, 2-{4-[4-cyclopropyl-2-(4-trifluoromethyl-phenyl)-pyrimidin-5-ylmethoxy]-naphthalen-2-yloxy}-2-methyl-propionic acid, 2-(4-{2-[4-cyclopropyl-2-(4-trifluoromethyl-phenyl)-pyrimidin-5-yl]-ethoxy}-naphthalen-2-yloxy)-2-methyl-propionic acid, 2-methyl-2-(4-{2-[2-methyl-6-(4-trifluoromethyl-phenyl)-pyridin-3-yl]-ethoxy}-naphthalen-2-yloxy)-propionic acid, and 2-methyl-2-{4-[2-methyl-6-(4-trifluoromethyl-phenyl)-pyridin-3-ylmethoxy]-naphthalen-2-yloxy}-propionic acid.

Compounds of formula I, wherein $R^{13}$ is aryl, are preferred. More preferred are those compounds of formula I, wherein $R^{13}$ is unsubstituted phenyl or phenyl substituted with one to three groups selected from $C_{1-7}$-alkyl, $C_{1-7}$-alkoxy, halogen, fluoro-$C_{1-7}$-alkyl and cyano, with those compounds, wherein $R^{13}$ is phenyl substituted with halogen or fluoro-$C_{1-7}$-alkyl, being particularly preferred. Especially preferred are those compounds, wherein $R^{13}$ is 4-trifluoromethylphenyl.

Also preferred are compounds of formula I according to the present invention having the formula

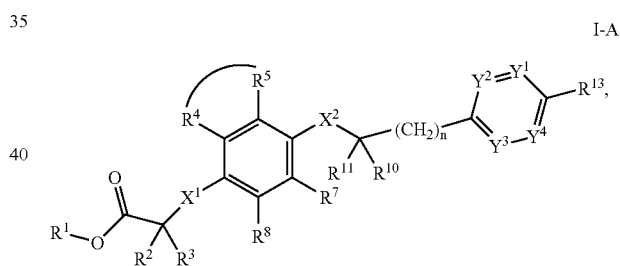

I-A wherein $R^4$ and $R^5$ form a ring together with the carbon atoms to which they are attached, and $R^4$ and $R^5$ together are:
—CH=CH—CH=CH—,
—CH=CH—S—, —S—CH=CH—, —CH=CH—O—, —O—CH=CH—,
—$(CH_2)_p$—, —O—$(CH_2)_q$— or —$(CH_2)_q$—O—,
wherein p is 3, 4 or 5 and q is 2 or 3; and
$X^1$, $X^2$, $Y^1$ to $Y^4$, $R^1$, $R^2$, $R^3$, $R^7$, $R^8$, $R^{10}$, $R^{11}$, $R^{13}$ and n are as defined in claim 1;
provided that compounds of formula I-A are excluded, wherein $X^1$ is O, $R^2$ and $R^3$ are hydrogen, $X^2$ is O or S and $R^{10}$ and $R^{11}$ are hydrogen.

Further preferred compounds of formula I are compounds having the formula

I-B

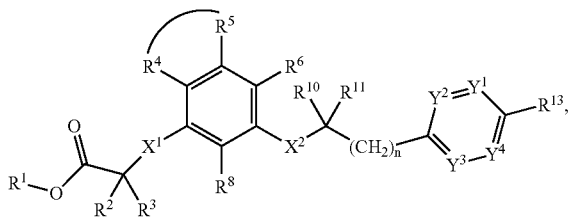

a pyridyl group. Especially preferred are those compounds of formula I, wherein $Y^1$ is N and $Y^2$, $Y^3$ and $Y^4$ are C—$R^{12}$, e.g. compounds of formula I containing the group

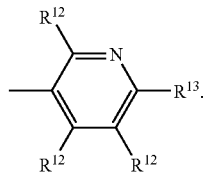

wherein
$R^4$ and $R^5$ form a ring together with the carbon atoms to which they are attached, and $R^4$ and $R^5$ together are:
—CH═CH—CH═CH—,
—CH═CH—S—, —S—CH═CH—, —CH═CH—O—, —O—CH═CH—,
—(CH$_2$)$_p$—, —O—(CH$_2$)$_q$— or —(CH$_2$)$_q$—O—,
wherein p is 3, 4 or 5 and q is 2 or 3; and
$X^1$, $X^2$, $Y^1$ to $Y^4$, $R^1$, $R^2$, $R^3$, $R^6$, $R^8$, $R^{10}$, $R^{11}$, $R^{13}$ and n are as defined in claim 1.

Furthermore, compounds of formula I having the formula

Further preferred compounds of the present invention are those, wherein 2 of $Y^1$, $Y^2$, $Y^3$ and $Y^4$ are N and the other ones are C—$R^{12}$, thus meaning compounds containing a pyrazinyl group or a pyrimidinyl group or a pyridazinyl group.

Especially preferred are compounds of formula I, wherein $Y^1$ and $Y^4$ are N and $Y^2$ and $Y^3$ are C—$R^2$, e.g. compounds of formula I containing the pyrimidinyl group

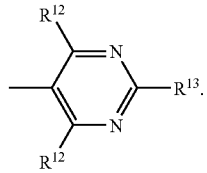

I-C

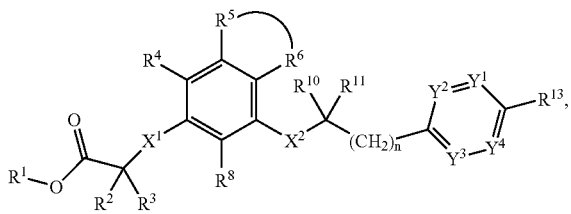

Also preferred are compounds of formula I, wherein $Y^1$ and $Y^3$ are N and $Y^2$ and $Y^4$ are C—$R^{12}$, e.g. compounds of formula I containing the pyrazinyl group

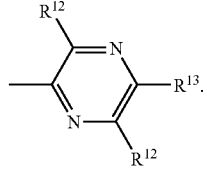

wherein
$R^5$ and $R^6$ form a ring together with the carbon atoms to which they are attached, and $R^5$ and $R^6$ together are:
—CH═CH—CH═CH—,
—CH═CH—S—, —S—CH═CH—, —CH═CH—O—, —O—CH═CH—,
—(CH$_2$)$_p$—, —O—(CH$_2$)$_q$— or —(CH$_2$)$_q$—O—,
wherein p is 3, 4 or 5 and q is 2 or 3; and
$X^1$, $X^2$, $Y^1$ to $Y^4$, $R^1$, $R^2$, $R^3$, $R^4$, $R^8$, $R^{10}$, $R^{11}$, $R^{13}$ and n are as defined in claim 1, are also preferred.

The integer n is 0, 1, or 2. Preferred compounds of formula I are those, wherein n is 0 or 1, more preferably n is 0.

$Y^1$, $Y^2$, $Y^3$ and $Y^4$ signify N or C—$R^{12}$, provided that 1 or 2 of $Y^1$, $Y^2$, $Y^3$ and $Y^4$ are N and the other ones are C—$R^{12}$. $R^{12}$ independently from each other in each occurrence is selected from hydrogen, $C_{1-7}$-alkyl, $C_{3-7}$-cycloalkyl, fluoro-$C_{1-7}$-alkyl, $C_{1-7}$-alkoxy-$C_{1-7}$-alkyl, hydroxy-$C_{1-7}$-alkyl, $C_{1-7}$-alkylthio-$C_{1-7}$-alkyl, carboxy-$C_{1-7}$-alkoxy-$C_{1-7}$-alkyl, carboxy-$C_{1-7}$-alkyl, mono- or di-$C_{1-7}$-alkyl-amino-$C_{1-7}$-alkyl, $C_{1-7}$-alkanoyl-$C_{1-7}$-alkyl, $C_{2-7}$-alkenyl, and $C_{2-7}$-alkinyl. Preferably, $R^{12}$ independently from each other in each occurance is selected from hydrogen, $C_{1-7}$-alkyl, $C_{3-7}$-cycloalkyl, fluoro-$C_{1-7}$-alkyl; $C_{1-7}$-alkoxy-$C_{1-7}$-alkyl, hydroxy-$C_{1-7}$-alkyl, and $C_{1-7}$-alkylthio-$C_{1-7}$-alkyl. More preferably, $R^{12}$ is selected from hydrogen, $C_{1-7}$-alkyl and $C_{3-7}$-cycloalkyl.

Preferred compounds of the present invention are for example those, wherein 1 of $Y^1$, $Y^2$, $Y^3$ and $Y^4$ is N and the other ones are C—$R^{12}$, thus meaning compounds containing $R^{12}$ is preferably hydrogen, $C_{1-7}$-alkyl, or $C_{3-7}$-cycloalkyl. Compounds of formula I, wherein $R^{12}$ is $C_{1-7}$-alkyl or $C_{3-7}$-cycloalkyl, are especially preferred.

Examples of preferred compounds of formula I are the following:

[rac]-[4-(methyl-{1-[2-methyl-6-(4-trifluoromethyl-phenyl)-pyridin-3-yl]-ethyl}-amino)-naphthalen-1-yloxy]-acetic acid;

[rac]-[4-(methyl-{1-[2-methyl-6-(3-trifluoromethyl-phenyl)-pyridin-3-yl]-propyl}-amino)-naphthalen-1-yloxy]-acetic acid;

[rac]-[4-(methyl-{1-[2-methyl-6-(3-trifluoromethyl-phenyl)-pyridin-3-yl]-butyl}-amino)-naphthalen-1-yloxy]-acetic acid;

[rac]-2-methoxy-3-(4-{2-[2-methyl-6-(4-trifluoromethyl-phenyl)-pyridin-3-yl]-ethoxy}-naphthalen-2-yl)-propionic acid;

3-{4-[2-methyl-6-(4-trifluoromethyl-phenyl)-pyridin-3-ylmethoxy]-5,6,7,8-tetrahydro-naphthalen-1-yl}-propionic acid;

3-{4-[2-methyl-6-(4-trifluoromethyl-phenyl)-pyridin-3-ylmethoxy]-naphthalen-1-yl}-propionic acid;

3-(4-{2-[2-methyl-6-(4-trifluoromethyl-phenyl)-pyridin-3-yl]-ethoxy}-5,6,7,8-tetrahydro-naphthalen-1-yl)-propionic acid;
3-(4-{2-[2-methyl-6-(4-trifluoromethyl-phenyl)-pyridin-3-yl]-ethoxy}-naphthalen-1-yl)-propionic acid;
3-{4-[4-cyclopropyl-2-(4-trifluoromethyl-phenyl)-pyrimidin-5-ylmethoxy]-naphthalen-1-yl}-propionic acid;
3-{4-[4-cyclopropyl-2-(4-trifluoromethyl-phenyl)-pyrimidin-5-ylmethoxy]-5,6,7,8-tetrahydro-naphthalen-1-yl}-propionic acid;
3-{4-[5-(4-trifluoromethyl-phenyl)-pyrimidin-2-ylmethoxy]-naphthalen-1-yl}-propionic acid;
[rac]-(4-{1-[2-methyl-6-(4-trifluoromethyl-phenyl)-pyridin-3-yl]-ethoxy}-naphthalen-1-yloxy)-acetic acid;
2-methyl-2-(4-{methyl-[2-methyl-6-(4-trifluoromethyl-phenyl)-pyridin-3-ylmethyl]-amino}-5,6,7,8-tetrahydro-naphthalen-1-yloxy)-propionic acid;
2-methyl-2-(3-{2-[2-methyl-6-(4-trifluoromethyl-phenyl)-pyridin-3-yl]-ethoxy}-naphthalen-1-yloxy)-propionic acid;
2-methyl-2-{3-[2-methyl-6-(4-trifluoromethyl-phenyl)-pyridin-3-ylmethoxy]-naphthalen-1-yloxy}-propionic acid;
2-(3-{2-[4-cyclopropyl-2-(4-trifluoromethyl-phenyl)-pyrimidin-5-yl]-ethoxy}-naphthalen-1-yloxy)-2-methyl-propionic acid;
2-{4-[4-cyclopropyl-2-(4-trifluoromethyl-phenyl)-pyrimidin-5-ylmethoxy]-naphthalen-2-yloxy}-2-methyl-propionic acid;
2-(4-{2-[4-cyclopropyl-2-(4-trifluoromethyl-phenyl)-pyrimidin-5-yl]-ethoxy}-naphthalen-2-yloxy)-2-methyl-propionic acid;
2-methyl-2-(4-{2-[2-methyl-6-(4-trifluoromethyl-phenyl)-pyridin-3-yl]-ethoxy}-naphthalen-2-yloxy)-propionic acid; and
2-methyl-2-{4-[2-methyl-6-(4-trifluoromethyl-phenyl)-pyridin-3-ylmethoxy]-naphthalen-2-yloxy}-propionic acid.

The following compounds are especially preferred:

[rac]-[4-(methyl-{1-[2-methyl-6-(3-trifluoromethyl-phenyl)-pyridin-3-yl]-butyl}-amino)-naphthalen-1-yloxy]-acetic acid;
[rac]-2-methoxy-3-(4-{2-[2-methyl-6-(4-trifluoromethyl-phenyl)-pyridin-3-yl]-ethoxy}-naphthalen-2-yl)-propionic acid;
3-{4-[2-methyl-6-(4-trifluoromethyl-phenyl)-pyridin-3-ylmethoxy]-5,6,7,8-tetrahydro-naphthalen-1-yl}-propionic acid;
3-{4-[4-cyclopropyl-2-(4-trifluoromethyl-phenyl)-pyrimidin-5-ylmethoxy]-naphthalen-1-yl}-propionic acid;
3-{4-[4-cyclopropyl-2-(4-trifluoromethyl-phenyl)-pyrimidin-5-ylmethoxy]-5,6,7,8-tetrahydro-naphthalen-1-yl}-propionic acid;
2-(3-{2-[4-cyclopropyl-2-(4-trifluoromethyl-phenyl)-pyrimidin-5-yl]-ethoxy}-naphthalen-1-yloxy)-2-methyl-propionic acid;
2-(4-{2-[4-cyclopropyl-2-(4-trifluoromethyl-phenyl)-pyrimidin-5-yl]-ethoxy}-naphthalen-2-yloxy)-2-methyl-propionic acid; and
2-methyl-2-(4-{2-[2-methyl-6-(4-trifluoromethyl-phenyl)-pyridin-3-yl]-ethoxy}-naphthalen-2-yloxy)-propionic acid.

Furthermore, the pharmaceutically acceptable salts of the compounds of formula I and the pharmaceutically acceptable esters of the compounds of formula I individually constitute preferred embodiments of the present invention.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluant). The invention embraces all of these forms.

It will be appreciated, that the compounds of general formula I in this invention may be derivatised at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula I as defined above, which process comprises reacting a compound of formula

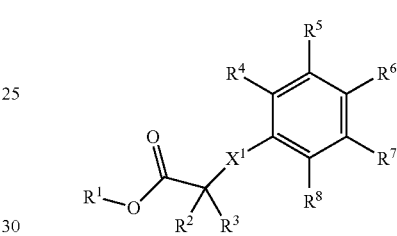

II wherein $R^1$ is $C_{1-7}$-alkyl, $R^2$ to $R^8$ are as defined above and $R^6$ or $R^7$ are selected from —OH, —SH or —NHR$^9$, wherein $R^9$ is as defined above, with a compound of formula

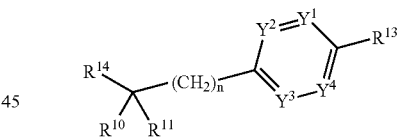

III wherein $Y^1$ to $Y^4$, $R^{10}$, $R^{11}$, $R^{13}$ and n are as defined above and $R^{14}$ is —OH, —Cl, —Br, —I or another leaving group, to obtain a compound of formula

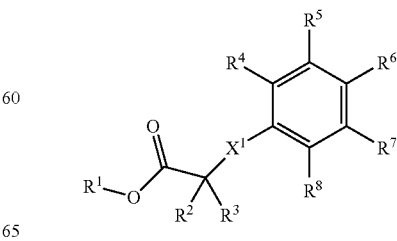

I wherein $R^6$ or $R^7$ is

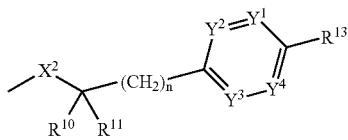

and wherein $X^2$ is O, S or $-NR^9$, $R^1$ is $C_{1-7}$-alkyl and $X^1$, $Y^1$ to $Y^4$, $R^2$ to $R^{13}$ and n are as defined above, and optionally hydrolysing the ester group to obtain a compound of formula I, wherein $R^1$ is hydrogen.

As described above, the compounds of formula (I) of the present invention can be used as medicaments for the treatment and/or prevention of diseases which are modulated by PPARδ and/or PPARα agonists. Examples of such diseases are diabetes, particularly non-insulin dependent diabetes mellitus, increased lipid and cholesterol levels, particularly low HDL-cholesterol, high LDL-cholesterol, or high triglyceride levels, atherosclerotic diseases, metabolic syndrome (syndrome X), obesity, elevated blood pressure, endothelial dysfunction, procoagulant state, dyslipidemia, polycystic ovary syndrome, inflammatory diseases (such as e.g. Crohn's disease, inflammatory bowel disease, colitis, pancreatitis, cholestasis/fibrosis of the liver, rheumatoid arthritis, osteoarthritis, psoriasis and other skin disorders, and diseases that have an inflammatory component such as e.g. Alzheimer's disease or impaired/improvable cognitive function) and proliferative diseases (cancers such as e.g. liposarcoma, colon cancer, prostate cancer, pancreatic cancer and breast cancer). The use as medicament for the treatment of low HDL cholesterol levels, high LDL cholesterol levels, high triglyceride levels, and the metabolic syndrome (syndrome X) is preferred.

The invention therefore also relates to pharmaceutical compositions comprising a compound as defined above and a pharmaceutically acceptable carrier and/or adjuvant.

Further, the invention relates to compounds as defined above for use as therapeutically active substances, particularly as therapeutic active substances for the treatment and/or prevention of diseases which are modulated by PPARδ and/or PPARα agonists. Examples of such diseases are diabetes, particularly non-insulin dependent diabetes mellitus, increased lipid and cholesterol levels, particularly low HDL-cholesterol, high LDL-cholesterol, or high triglyceride levels, atherosclerotic diseases, metabolic syndrome (syndrome X), obesity, elevated blood pressure, endothelial dysfunction, procoagulant state, dyslipidemia, polycystic ovary syndrome, inflammatory diseases such as rheumatoid arthritis, osteoarthritis, psoriasis and other skin disorder, and proliferative diseases.

In another embodiment, the invention relates to a method for the treatment and/or prevention of diseases which are modulated by PPARδ and/or PPARα agonists, which method comprises administering a compound of formula (I) to a human or animal. Preferred examples of such diseases are diabetes, particularly non-insulin dependent diabetes mellitus, increased lipid and cholesterol levels, particularly low HDL-cholesterol, high LDL-cholesterol, or high triglyceride levels, atherosclerotic diseases, metabolic syndrome (syndrome X), obesity, elevated blood pressure, endothelial dysfunction, procoagulant state, dyslipidemia, polycystic ovary syndrome, inflammatory diseases such as rheumatoid arthritis, osteoarthritis, psoriasis and other skin disorder, and proliferative diseases.

The invention further relates to the use of compounds as defined above for the treatment and/or prevention of diseases which are modulated by PPARδ and/or PPARα agonists. Preferred examples of such diseases are diabetes, particularly non-insulin dependent diabetes mellitus, increased lipid and cholesterol levels, particularly low HDL-cholesterol, high LDL-cholesterol, or high triglyceride levels, atherosclerotic diseases, metabolic syndrome (syndrome X), obesity, elevated blood pressure, endothelial dysfunction, procoagulant state, dyslipidemia, polycystic ovary syndrome, inflammatory diseases such as rheumatoid arthritis, osteoarthritis, psoriasis and other skin disorder, and proliferative diseases.

In addition, the invention relates to the use of compounds as defined above for the preparation of medicaments for the treatment and/or prevention of diseases which are modulated by PPARδ and/or PPARα agonists. Preferred examples of such diseases are diabetes, particularly non-insulin dependent diabetes mellitus, increased lipid and cholesterol levels, particularly low HDL-cholesterol, high LDL-cholesterol, or high triglyceride levels, atherosclerotic diseases, metabolic syndrome (syndrome X), obesity, elevated blood pressure, endothelial dysfunction, procoagulant state, dyslipidemia, polycystic ovary syndrome, inflammatory diseases such as rheumatoid arthritis, osteoarthritis, psoriasis and other skin disorder, and proliferative diseases. Such medicaments comprise a compound as defined above.

The compounds of formula I can be manufactured by the methods given below, by the methods given in the examples or by analogous methods. Appropriate reaction conditions for the individual reaction steps are known to a person skilled in the art. Starting materials are either commercially available or can be prepared by methods analogous to the methods given below, by methods described in references cited in the text or in the examples, or by methods known in the art.

The compounds of formula I can be manufactured by the methods given below, by the methods given in the examples or by analogous methods. Appropriate reaction conditions for the individual reaction steps are known to a person skilled in the art. Starting materials are either commercially available or can be prepared by methods analogous to the methods given below, by methods described in references cited in the text or in the examples, or by methods known in the art.

The synthesis of compounds with the general structure I, particularly compounds according to formula Ia to Im, are described in scheme 1 to scheme 5. Scheme 6 to scheme 9 describe the synthesis of heterocycles 5 (scheme 1), identical to 11 (scheme 3), 8 (scheme 4) and 8 (scheme 5).

The synthesis of compounds with the general structure I, particularly compounds according to formula Ia with $X^1$ and $X^2$ equal to oxygen can be accomplished according to scheme 1.

Scheme 1

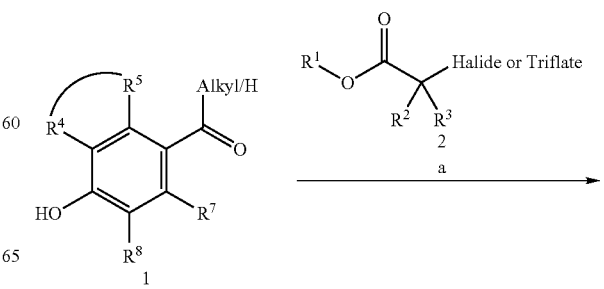

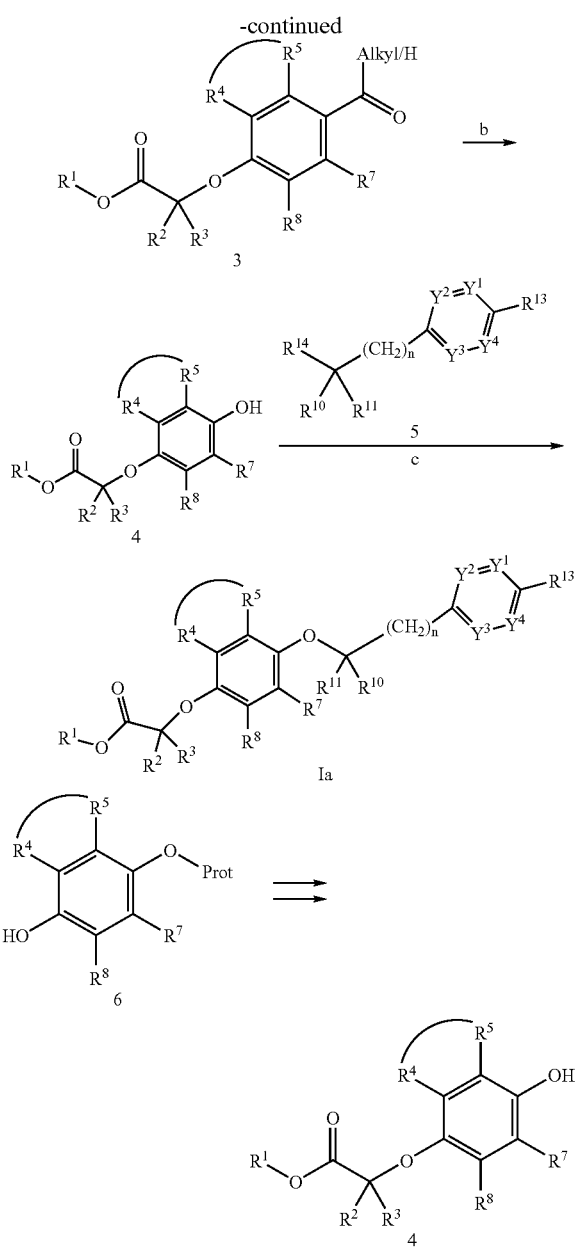

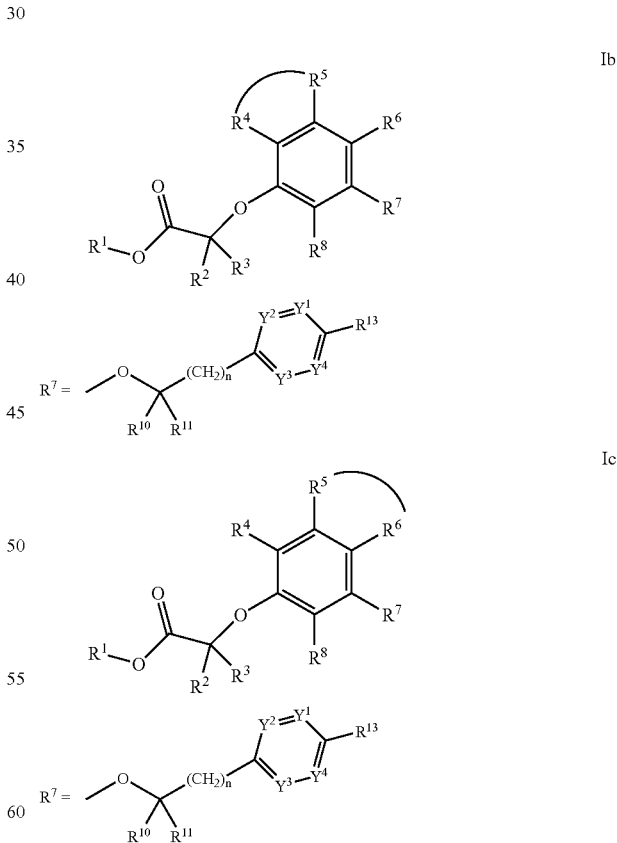

diethyl-azodicarboxylate as reagents; this transformation is preferably carried out in a solvent like toluene, dichloromethane or tetrahydrofuran at ambient temperature. Alternatively, if $R^{14}$ represents a halide, mesylate, tosylate or triflate moiety, the heterocycles 5 can be reacted with phenols 4 in solvents like N,N-dimethylformamide, dimethylsulfoxide, acetonitrile, acetone or methyl-ethyl ketone in the presence of a weak base like cesium or potassium carbonate at a temperature ranging from room temperature to 140° C., preferably around 50° C. to yield ether compounds Ia (step c). Those can optionally be hydrolyzed according to standard procedures, e. g. by treatment with an alkali hydroxide like LiOH or NaOH in a polar solvent mixture like tetrahydrofuran/ethanol/water leading to carboxylic acids Ia. Alternatively, compounds 4 can be prepared from suitably mono-protected precursors 6 carrying e.g. a benzyl-, a methoxycarbonyl, or a SEM-[(2-trimethylsilanyl-ethoxymethoxy)-] protective function. Such precursors 6 are known or can be prepared using methods well known in the art. Reaction with alpha halo esters as described for compounds 1 and subsequent removal of the protective function leads to compounds 4.

An analogous reaction scheme with the same reaction sequences applies for the isomeric two compound series leading to compounds of general formula I, particularly compounds according to formula Ib and Ic:

Hydroxy aldehydes or hydroxy aryl alkyl ketones 1, wherein $R^4$ and $R^5$ are bonded to each other to form a ring together with the carbon atoms to which they are attached, are known or can be prepared by methods known in the art [see e.g. Int. Patent Appl. (2002), 179 pp. WO 02/92084 A1]. Reaction of phenols 1 with alpha halo esters compounds 2 in the presence of a base like potassium or cesium carbonate in solvents like acetone, methyl-ethyl ketone, acetonitrile or N,N-dimethylformamide in a temperature range between room temperature and 140° C. leads to the corresponding ether compounds 3 (steps a). Baeyer Villiger oxidation e.g. with meta chloro perbenzoic acid in a solvent like dichloromethane, leads to compounds 4 (step b). Heterocycles 5 (prepared as outlined in schemes 6 to 9) are condensed with phenols 4 according to well known procedures (step c): if $R^{14}$ represents a hydroxy group e.g. via Mitsunobu-reaction, with triphenylphosphine and di-tert-butyl-, diisopropyl- or The synthesis of compounds with the general structure I, particularly compounds according to formula Id, with $X^1$ equal to O and $X^2$ equal to nitrogen can be accomplished according to schemes 2 and 3.

Scheme 2

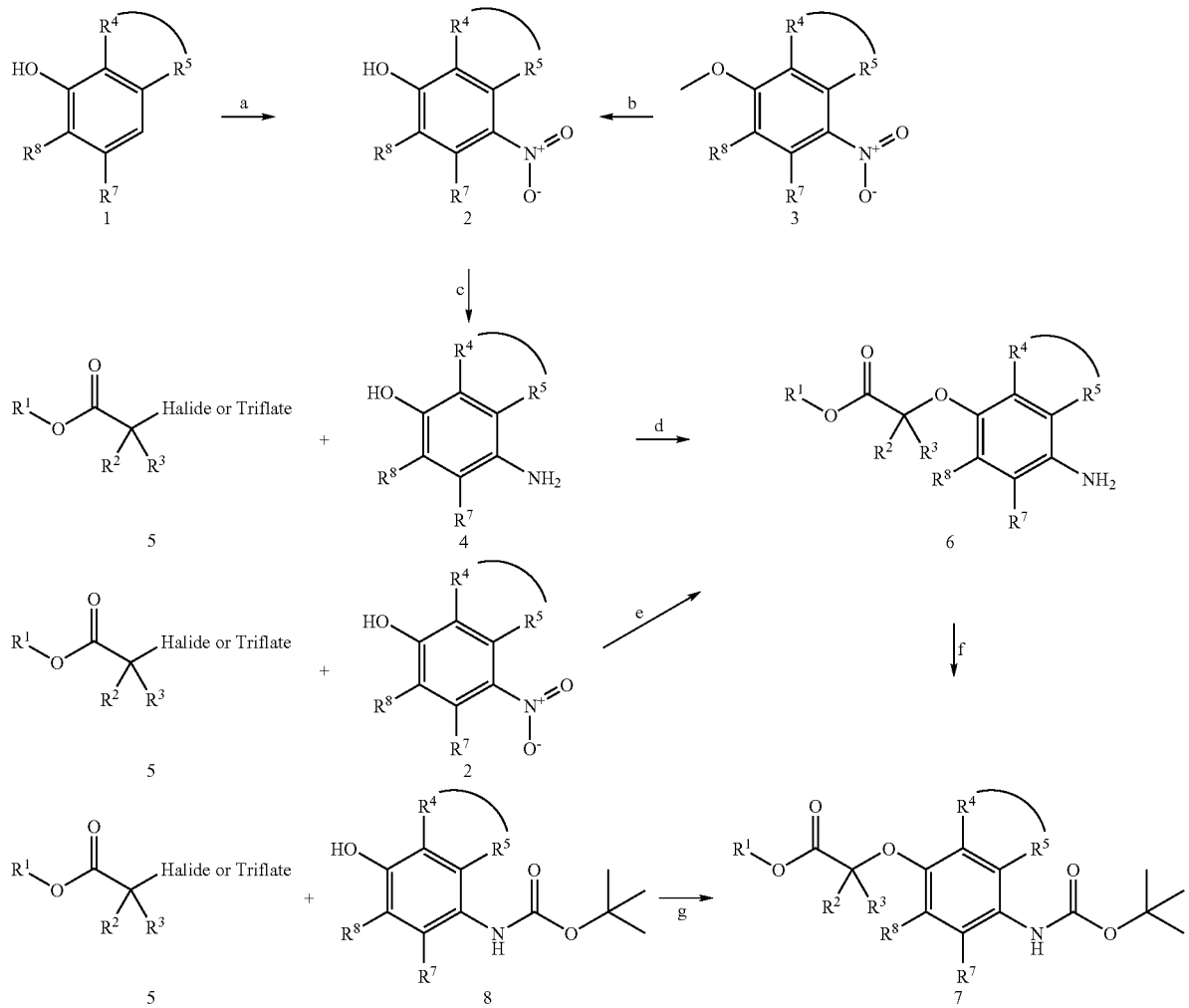

Nitro-phenols 2 of scheme 2, wherein $R^4$ and $R^5$ are bonded to each other to form a ring together with the carbon atoms to which they are attached, are commercial available, or known or can be synthesized from anisols 3 by demethylation with aqueous 62% HBr in acetic acid between RT and 120° C. (step b). Alternatively, phenols 1 can be nitrated in para-position according to well established methods, e.g. with a solution of $NaNO_3$ in water/concentrated hydrochloric acid in a solvent like $Et_2O$, followed by the addition of acetic acid anhydride at RT [following a procedure of P. Keller, *Bull. Soc. Fr.* 1994, 131, 27-29] leading to phenols 2 (step a). Nitro-phenols 2 are then hydrogenated in an alcohol like EtOH or MeOH with hydrogen in the presence of Pd/C and optionally an acid like HCl or AcOH at RT to give anilines 4 (step c). Intermediates 4 are then alkylated at oxygen with an activated ester compound 5, e.g. a bromo-acetate 5, in the presence of $K_2CO_3$ or $Cs_2CO_3$ in a solvent like acetonitrile or acetone between 10° C. and RT to give intermediates 6 of scheme 2 (step d). Activated esters 5 are commercial available or can be synthesized by methods known in the art. Triflates 5 can be prepared from the corresponding alcohols. Anilines 6 can alternatively be synthesized from compounds 5 and nitro-phenols 2 in a two step procedure: first by O-alkylation as described above, followed by hydrogenation with Pd/C in an alcohol like MeOH or EtOH optionally in the presence of AcOH or HCl (step e). BOC-protection with di-tert-butyl dicarbonate in tetrahydrofuran at RT to reflux yields compound 7 (step f). Compound 7 can also be synthesized directly from esters 5 and BOC-protected aniline 8 with $K_2CO_3$ or $Cs_2CO_3$ as described for the synthesis of compounds 6 (step g).

Scheme 3

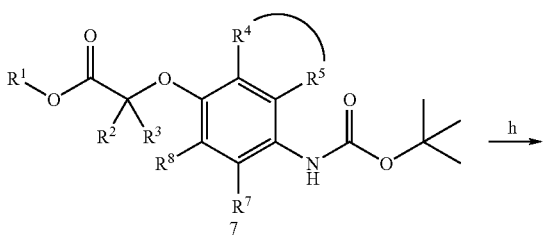

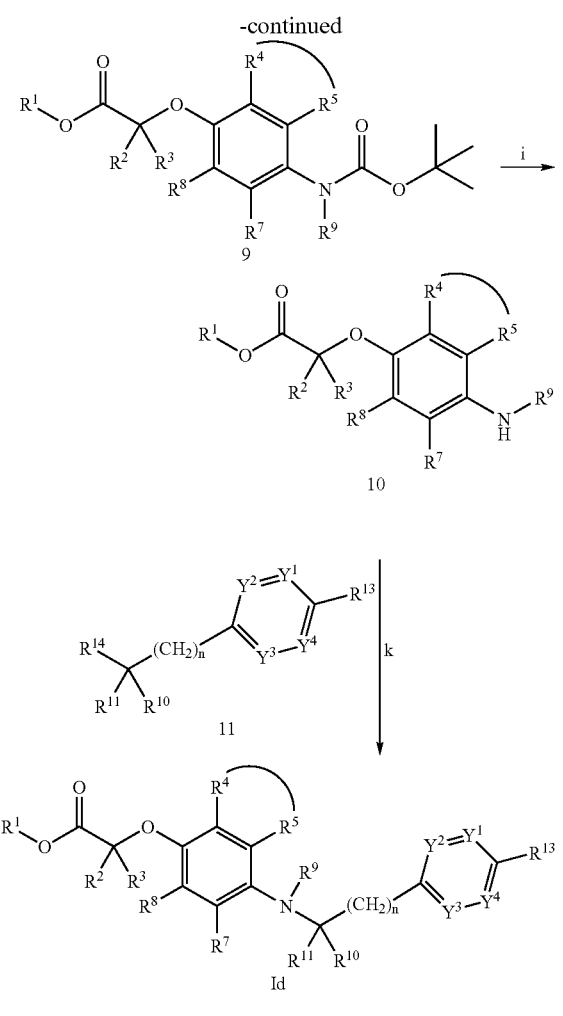

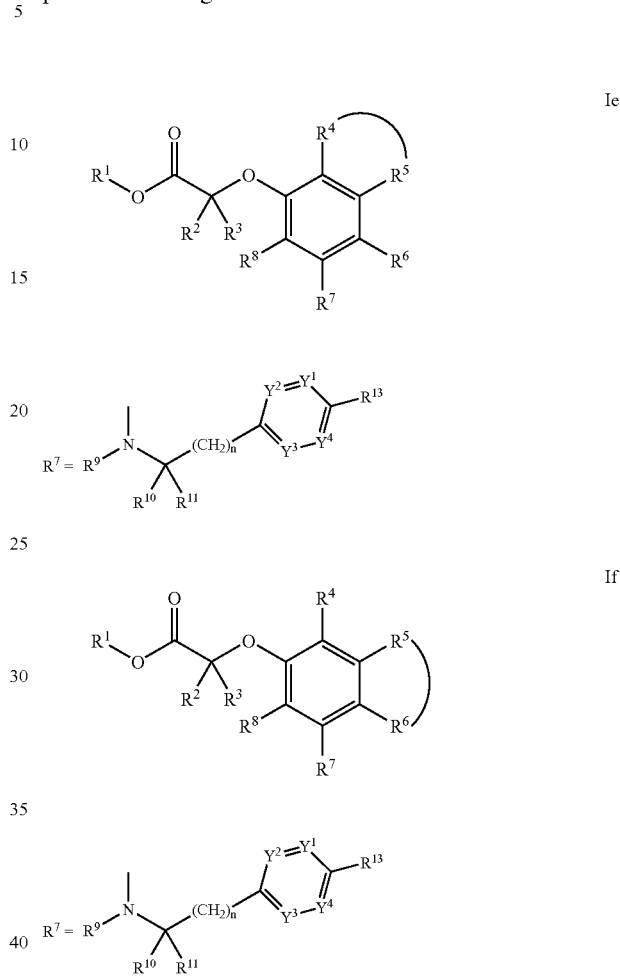

Intermediates 7 of scheme 3 can optionally be alkylated at nitrogen using sodium hydride and a reactive alkyl halogenide/mesylate or triflate to give compounds 9 (step h, scheme 3). Standard BOC-deprotection (TFA/CH$_2$Cl$_2$, or HCl in dioxane) at 0° C. to RT affords anilines 10 of (step i, scheme 3). Reaction with activated heterocycles 11($R^{14}$ being a halide or a methanesulfonate) using sodium hydride or sodium, potassium or cesium carbonate in N,N-dimethylformamide, dimethylsulfoxide, dimethylacetamide or tetrahydrofuran, at 0° C. to RT, leads to compounds Id (step k). Alternatively, heterocycles 11 with $R^{14}$=OH can be transformed in situ to the coresponding triflate by treatment with trifluoromethanesulfonic anhydride/2,6-di-tert-butylpyridine in CH$_2$Cl$_2$ at 0° C. This triflate is then reacted with anilines 10 in the presence of 2,6-di-tert-butylpyridine as base in nitromethane between RT and 60° C. to yield compounds Id [following a procedure of Belostotskii, Anatoly M., Hassner, A., Tetrahedron Lett. 1994, 35(28), 5075-6) (step k). Secondary aniline compounds Id ($R^9$=H) can be reductively methylated with an aqueous solution of NaH$_2$PO$_3$ and formaldehyde between RT and 65° C. [Loibner, H., Pruckner, A., Stuetz, A., Tetrahedron Lett. 1984, 25, 2535-2536] to give compounds Id with $R^9$=Me. Ensuing hydrolysis with aqueous LiOH, NaOH or KOH in tetrahyrofuran/EtOH or another suitable solvent produces compounds Id of scheme 3 in the form of the free acid.

An analogous reaction scheme with the same reaction sequences applies for the two isomeric compound series leading to compounds of general formula I, particularly compounds according to formula Ie and If:

As alternative to the sequences described in scheme 2, the nitrogen containing intermediates can be prepared from suitable intermediates carrying a phenolic hydroxyl moiety. In such intermediates, optionally carrying one or more protective functions, the phenolic OH group can be replaced by the corresponding aromatic NH$_2$ function by methods known in the art. For example by a three step sequence as described in Tetrahedron Letters 43(42), 7617-7619(2002): i) transformation of the phenol moiety into its trifluoromethanesulfonate (triflic anhydride, 2,6-lutidine, 4-dimethylaminopyridine, dichloromethane, 0° C. to room temperature; ii) treatment of the triflate with benzophenone imine, di-palladium-tris (dibenzylideneacetone) complex, S-(–)-2,2'-bis(diphenylphosphino)-1,1'-binaphthyl, cesium carbonate, toluene, in a Schlenk tube at temperatures around 120° C.; iii) treatment with catalytic amounts of hydrochloric acid in wet tetrahydrofuran preferably at room temperature to liberate the aromatic NH$_2$ moiety.

The synthesis of compounds with the general structure I, particularly compounds according to formula Ig, with $X^1$ equal to CH$_2$ and $X^2$ equal to oxygen can be accomplished according to schemes 4.

Scheme 4

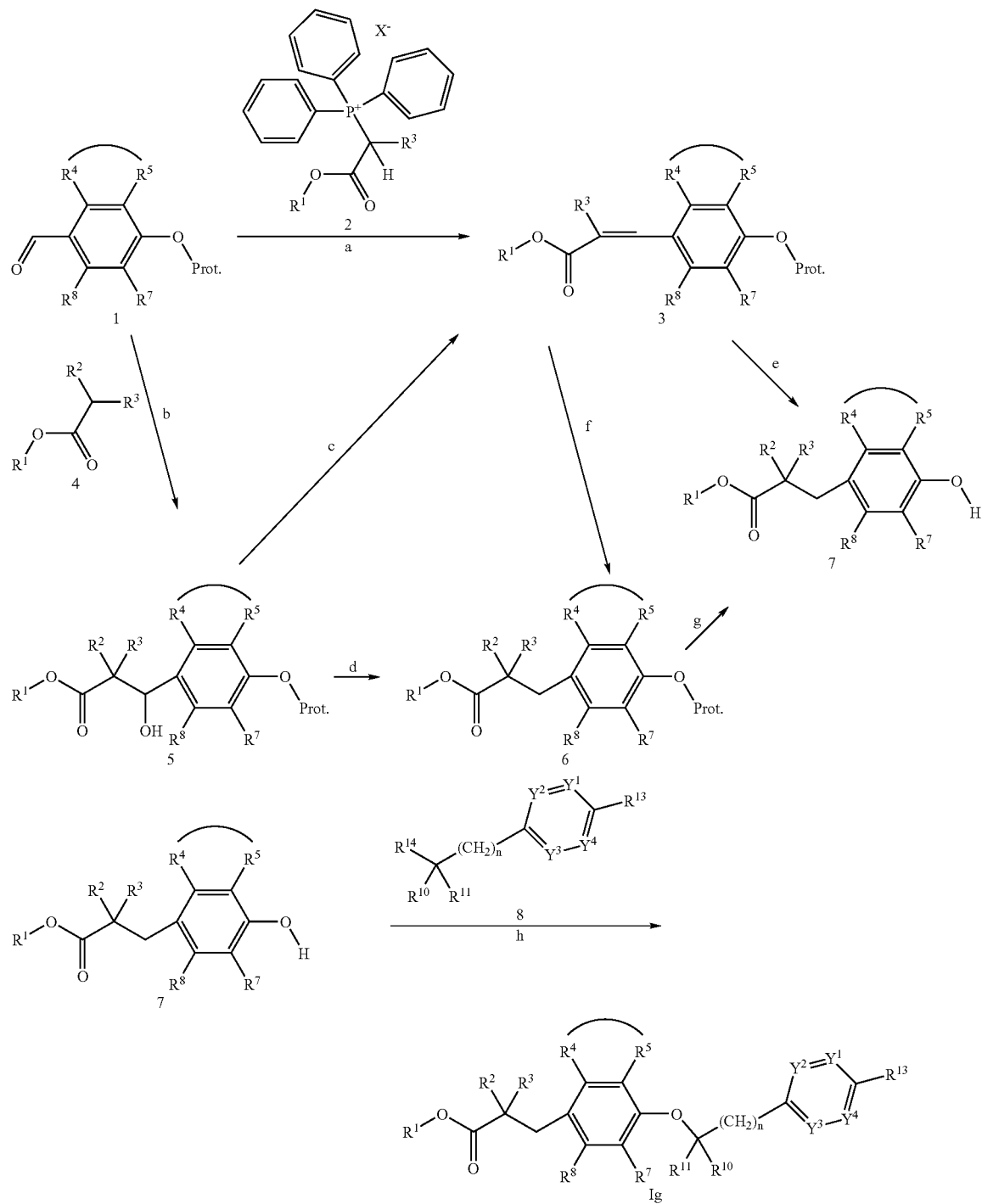

Aldehydes 1 wherein $R^4$ and $R^5$ are bonded to each other to form a ring together with the carbon atoms to which they are attached, are known or can be prepared by methods known in the art [see e.g. Int. Patent Appl. (2002), 179 pp. WO 02/92084 A1]. Aldehydes 1 can be reacted with a Wittig salt 2 such as (1,2-diethoxy-2-oxoethyl)triphenyl phosphonium chloride or (1,2-dimethoxy-2-oxoethyl)triphenyl phosphonium bromide in solvents like isopropanol, dichloromethane or tetrahydrofuran or mixtures thereof in the presence of a base like potassium carbonate, 1,8-diazabicyclo[5.4.0] undec-7-ene (DBU), 1,1,3,3-tetramethyl-guanidine or sodium tert butylate, preferably between 0° C. and the reflux temperature of the solvents, giving acrylic esters 3 as E and/or Z isomers (step a). Alternatively, a Horner-Emmons reaction can be used for the transformation of compounds 1 into unsaturated esters 3, e.g. using dimethyl(methoxycarbonyl)methyl phosphonate, optionally substituted at the methylene group, a base like sodium hydride in a solvent like tetrahydrofuran or 1,2-dimethoxy ethane. Hydrogenation of acrylic esters 3 using palladium on charcoal as catalyst, preferably at room temperature and 1 atm. pressure of hydrogen, in solvents like methanol, ethanol, tetrahydrofuran, acetic acid, dichloromethane and mixtures thereof, affords esters 7, provided that the protecting group can be cleaved reductively (step e).

Alternatively, aldehydes 1 are reacted with the enolate of an acetic acid esters 4 (preferably the lithium-enolate, prepared at −78° C. by treatment of 4 with a strong, non-nucleophilic base like lithium diisopropylamide in an inert solvent like tetrahydrofuran), preferably at temperatures around −78° C., in solvents like tetrahydrofuran giving the aldol product 5 as a mixture of diasteromers (step b). Removal of the benzylic hydroxy group in compounds 5 can be performed with a reducing agent like e.g. triethylsilane in the presence of a Lewis acid, like boron-trifluoride, or a protic acid, like trifluoroacetic acid, in a suitable solvent like trifluoroacetic acid itself or dichloromethane between 0° C. and 60° C. to yield protected phenol compounds 6 (step d). Subsequent removal of the protecting group, e.g. a benzyl group, by standard technology, e.g. catalytic hydrogenation using hydrogen and a catalyst like palladium or by using dimethyl sulfide and boron trifluoride diethyl etherate in a solvent like dichloromethane between room temperature and the reflux temperature of the solvent gives phenolic compounds 7 (step g). Catalytic hydrogenation can be used to transform unsaturated esters 3 into compounds 6 (step f). In case the protective group in compounds 3 is a benzyl group, then a one step hydrogenation procedure directly gives phenolic compounds 7. Catalytic hydrogenation can also be used for the simultaneous removal of the benzylic hydroxy function and a benzyl protecting group, preferably using palladium on charcoal as catalyst in the presence of an acid like oxalic acid in solvents like alcohols at temperatures around room temperature and a hydrogen pressure up to 100 bar, thus giving the transformation of compounds 5 into compounds 7 in one step (step d and g). As an alternative method, compounds 5 can be treated with catalytic amounts of an acid like para toluene sulfonic acid in a solvent like benzene or toluene, preferably under conditions allowing the removal of the water formed (e.g. with a Dean Stark trap or in the presence of molecular sieves) at temperatures between room temperature and the reflux temperature of the solvents to yield acrylic esters 3 (step c). The condensation of phenols 7 with heterocycles 8 to form compounds Ig can be performed as outlined in scheme 1.

An analogous reaction scheme with the same reaction sequences applies for the two isomeric compound series leading to compounds of general formula I, particularly compounds according to formula Ih and Ii:

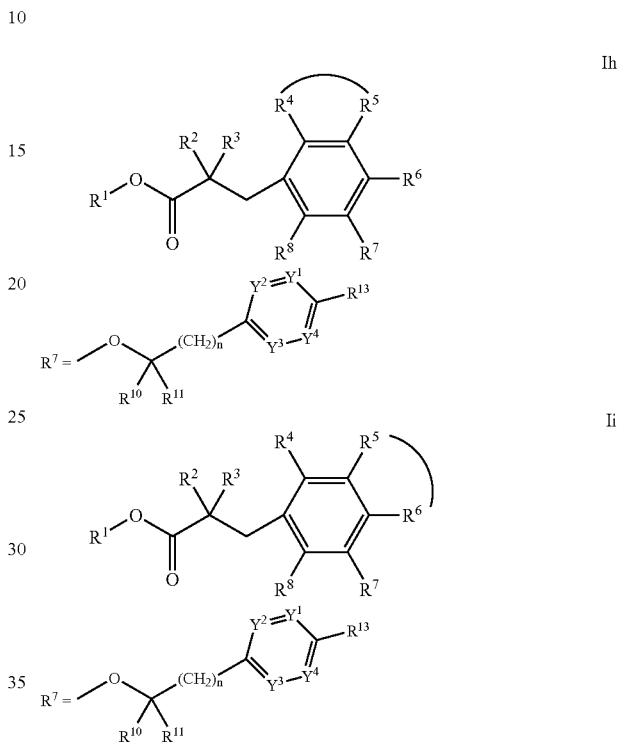

The synthesis of compounds with the general structure I, particularly compounds according to formula Ik, with $X^1$ equal to $CH_2$ and $X^2$ equal to nitrogen can be accomplished according to schemes 5.

Scheme 5

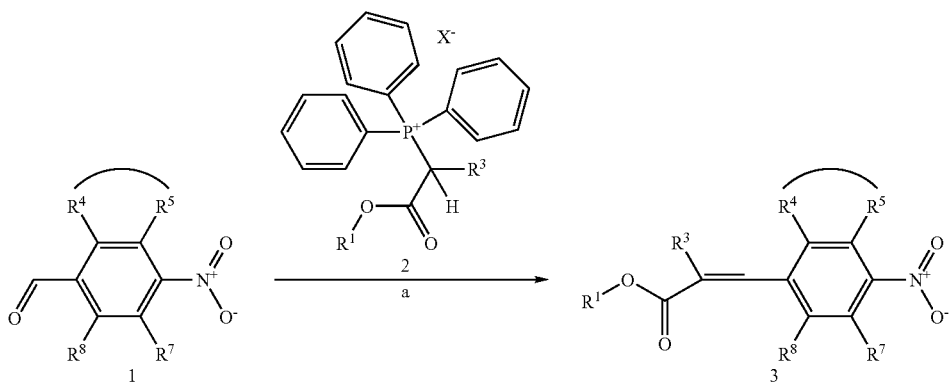

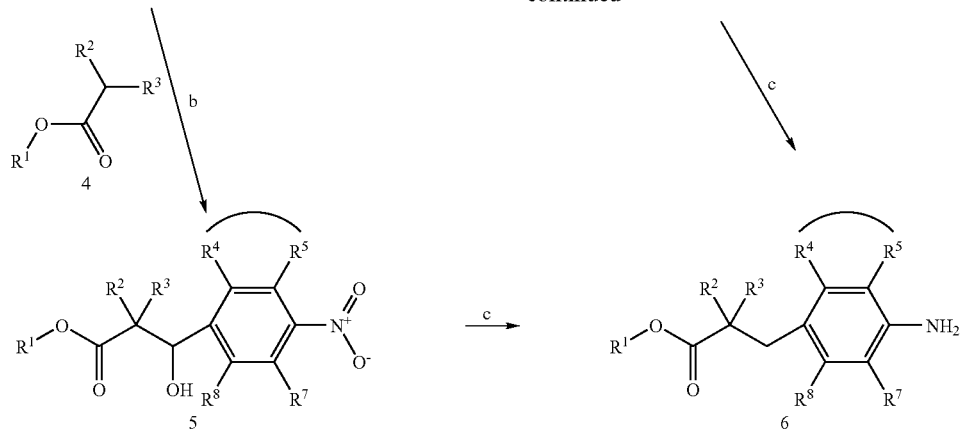

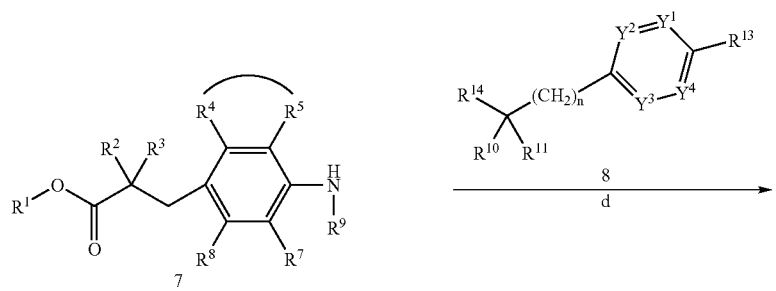

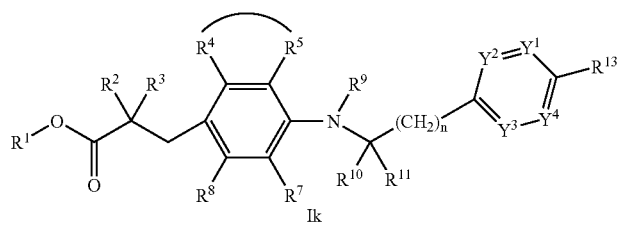

Nitro-phenyl compounds 3 and 5 are prepared from nitro aldehydes 1, which are known, commercially available or can be prepared by methods known in the art) by Wittig/Horner-Emmons or aldol reactions analogous to the reactions described for the synthesis of compounds 3 and 5 in scheme 4 (steps a and b). Catalytic hydrogenation can be used for the simultaneous removal of the benzylic hydroxy function (compounds 5) or the reduction double bond (compounds 3) and the reduction of the nitro group, preferably using palladium on charcoal as catalyst optionally in the presence of an acid like oxalic acid in solvents like alcohols at temperatures around room temperature and a hydrogen pressure up to 100 bar (step c). Compounds 7 with $R^9$ substituents different from hydrogen are obtained by first introduction of a BOC group, alkylation and removal of the BOC protective function as described in schemes 2 and 3. The condensation of anilines 7 with heterocycles 8 to form compounds Ik can be performed as outlined in scheme 3.

An analogous reaction scheme with the same reaction sequences applies for the isomeric two compound series leading to compounds of general formula I, particularly compounds according to formula Il and Im:

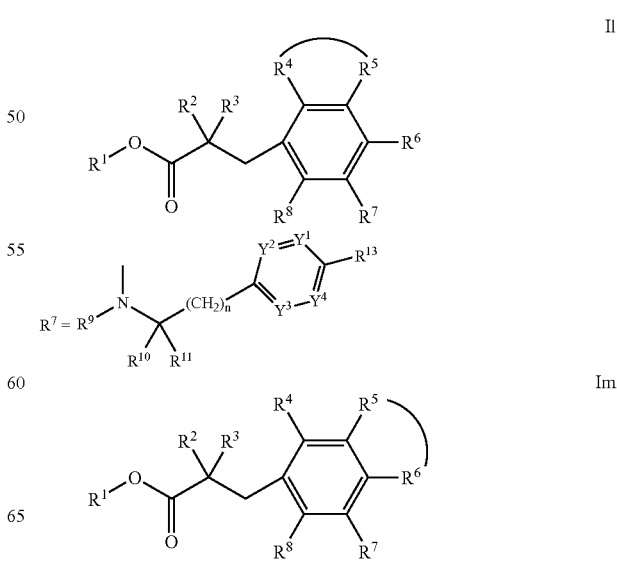

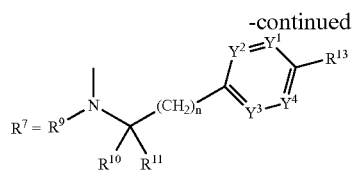

As alternative to the sequences described in scheme 5, the nitrogen containing intermediates can be prepared from suitable intermediates carrying a phenolic hydroxyl function. In such intermediates, optionally carrying one or more protective functions, the phenolic OH group can be replaced by the corresponding aromatic $NH_2$ function by methods known in the art. For example by a three step sequence as described in Tetrahedron Letters 43(42), 7617-7619(2002) and discussed in the context of schemes 2 and 3.

The synthesis of compounds with the general structure I, particularly compounds with $X^1$ and/or $X^2$ equal to S can be accomplished in close analogy to the synthesis of the corresponding analogues with $X^1$ and/or $X^2$ equal to oxygen. Suitable sulfur containing intermediates are known, can be prepared by methods known in the art or are prepared from phenolic intermediates as described by W Zhi-Liang and AP Kozikowski (J. Org. Chem. 2003, web publication release Oct. 10, 2003): treatment of a phenolic intermediate with sodium thiocyanate, sodium bromide and bromine is a solvent like methanol preferably between 0° C. and room temperature gives the corresponding 4-thiocyanatophenols; subsequent reduction with lithiumaluminium hydride in a solvent like tetrahydrofuran at temperatures around 0° C. then liberates the corresponding 4-mercapto-phenol. Alternatively, intermediates carrying an aromatic SH moiety can be prepared from suitable intermediates carrying a phenolic hydroxyl function In such intermediates, optionally carrying one or more protective functions, the phenolic OH group can be replaced by the corresponding phenolic SH function by methods known in the art. For example by a three step sequence as described in J. Labelled Compounds & Radiopharmaceuticals 43(7), 683-691, 2000: i) transformation of the phenol moiety into its trifluoromethanesulfonate (triflic anhydride, triethylamine, dichloromethane, at low temperature, preferably around −30° C.); ii) treatment of the triflate with triisopropylsilanethiolate, tetrakis(triphenylphosphine)-palladium(0) in solvent mixtures like toluene and tetrahydrofuran in a temperature range between 60° C. and 150° C.; iii) treatment of the silyl sulfide with hydrogen chloride in methanol preferably around 0° C. to liberate the phenolic SH moiety.

Compounds of the general formula I may be obtained in the form of racemates. Racemic compounds can be separated into their antipodes by methods known in the art, such as separation of the antipodes via diastereomeric salts by crystallization with optically pure amines such as e.g. (R) or (S)-1-phenyl-ethylamine, (R) or (S)-1-naphthalen-1-yl-ethylamine, brucine, quinine or quinidine or by separation of the antipodes by specific chromatographic methods using either a chiral adsorbens or a chiral eluent.

Scheme 6 to scheme 9 describe the synthesis of heterocycles 5 (scheme 1), identical to 11 (scheme 3), 8 (scheme 4) and 8 (scheme 5).

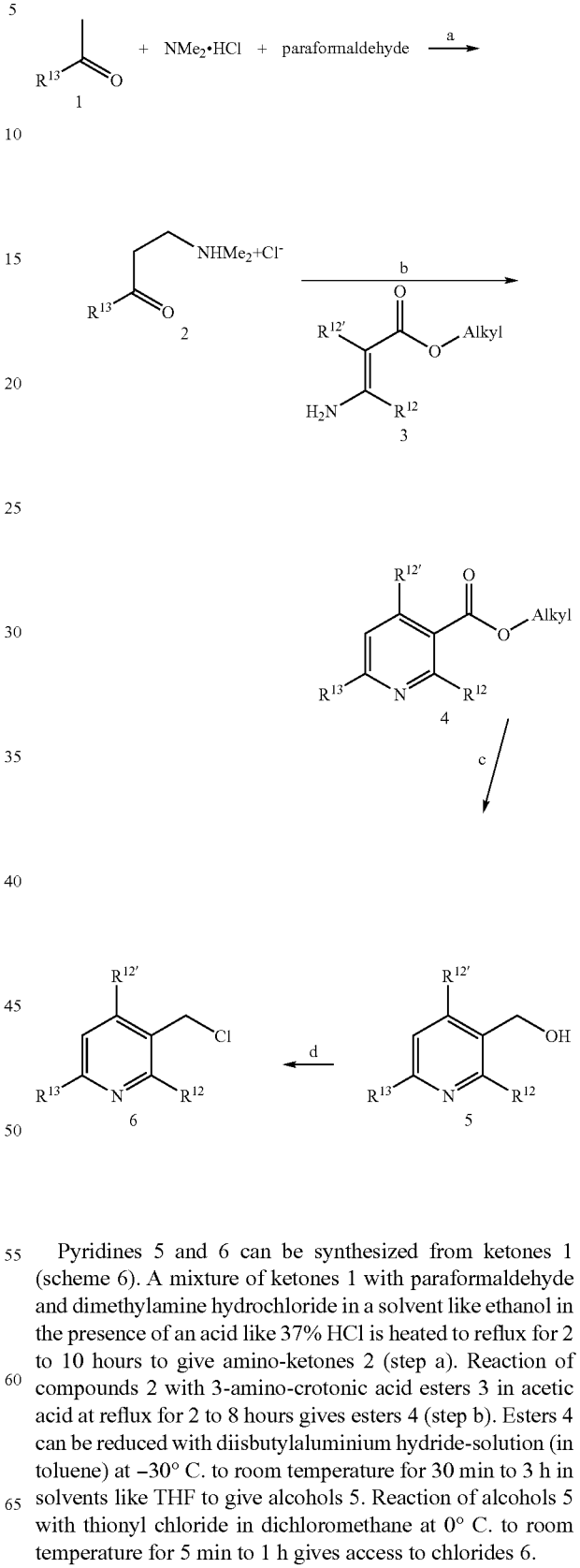

Pyridines 5 and 6 can be synthesized from ketones 1 (scheme 6). A mixture of ketones 1 with paraformaldehyde and dimethylamine hydrochloride in a solvent like ethanol in the presence of an acid like 37% HCl is heated to reflux for 2 to 10 hours to give amino-ketones 2 (step a). Reaction of compounds 2 with 3-amino-crotonic acid esters 3 in acetic acid at reflux for 2 to 8 hours gives esters 4 (step b). Esters 4 can be reduced with diisbutylaluminium hydride-solution (in toluene) at −30° C. to room temperature for 30 min to 3 h in solvents like THF to give alcohols 5. Reaction of alcohols 5 with thionyl chloride in dichloromethane at 0° C. to room temperature for 5 min to 1 h gives access to chlorides 6.

Scheme 7

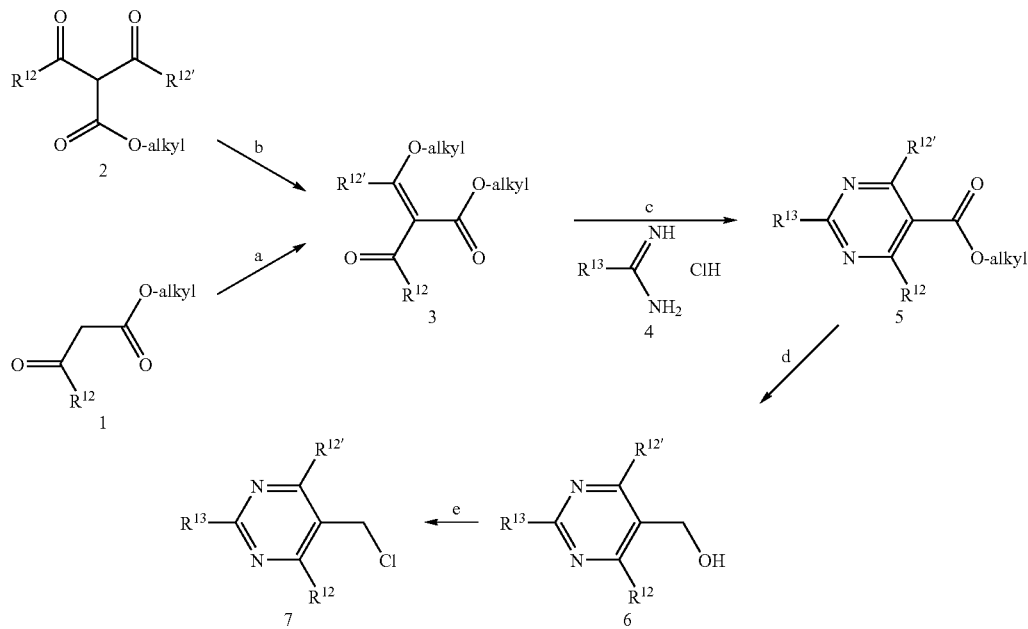

The synthesis of chlormethyl pyrimidines 7 and pyrimidine methanol compounds 6 is described in scheme 7. Reaction of 3-oxo-esters 1 with triethyl orthoformate in acetic anhydride at room temperature to reflux for 1 to 8 hours gives an E/Z mixture of the 3-ethoxy-acrylic acid esters 3 (step a). Diketo-esters 2 are reacted with methyl triflate in the presence of cesium carbonate in acetonitrile to give O-methylated products 3 (step b) [S. W. McCombie et al. Bioorganic & Medicinal Chemistry Letters 13 (2003) 567-571], thus yielding substituted enolethers 3 ($R^{12'}$ not H). Reaction with amidine hydrochlorides 4 in ethanol in the presence of alkali tert-butoxide at room temperature gives access to esters 5 (step c). Esters 5 can be reduced with diisobutylaluminium hydride-solution (in toluene) at −30° C. to room temperature for 30 min to 3 h in solvents like THF to give alcohols 6 (step d). Reaction of alcohols 6 with thionyl chloride in dichloromethane at 0° C. to room temperature for 5 min to 1 h gives access to chlorides 7 (step e).

Scheme 8

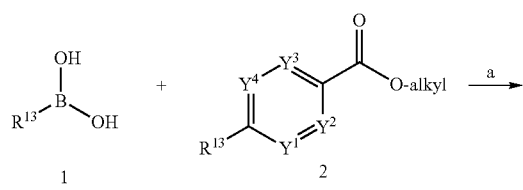

-continued

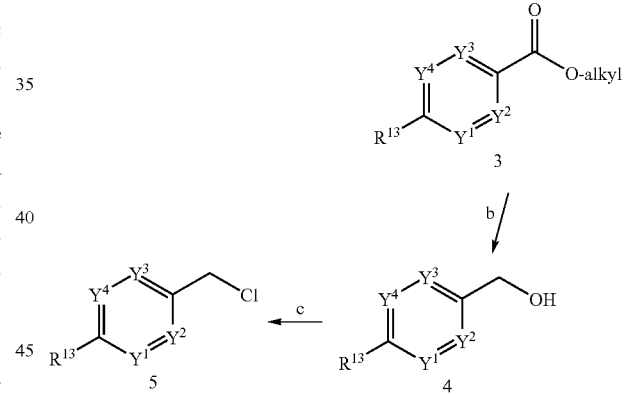

A general synthesis for alcohols 4 and chlorides 5 is depicted in scheme 8. Suzuki-coupling with boronic acides 1 and 6-halo-pyridazine-3-carboxylic acid esters 2,5-halopyrazine-2-carboxylic acid esters 2,6-halo-nicotinic acid esters 2,5-halo-pyridine-2-carboxylic acid esters 2,2-halopyrimidine-5-carboxylic acid esters 2 or 5-halo-pyrimidine-2-carboxylic acid esters 2 with $Pd(PhP)_4$ or $PdCl_2(dppf)$ [(1,1'-bis(diphenylphosphino)ferrocene)-dichloropalladium(II) $\times CH_2Cl_2$ (1:1)] in toluene, dimethoxyethane, ethanol or DMF with cesium carbonate, potassium carbonate or cesium fluoride at room temperature to 90° C. for 2 to 8 h give esters 3 (step a). Esters 2 are either commercially available or can be prepared by methods known to a person skilled in the art. Esters 3 can be reduced with diisobutylaluminium hydride-solution (in toluene) at −30° C. to room temperature for 30 min to 3 h in solvents like THF to give alcohols 4 (step d). Reaction of alcohols 4 with thionyl chloride in dichloromethane at 0° C. to room temperature for 5 min to 1 h gives access to chlorides 5 (step c).

Scheme 9

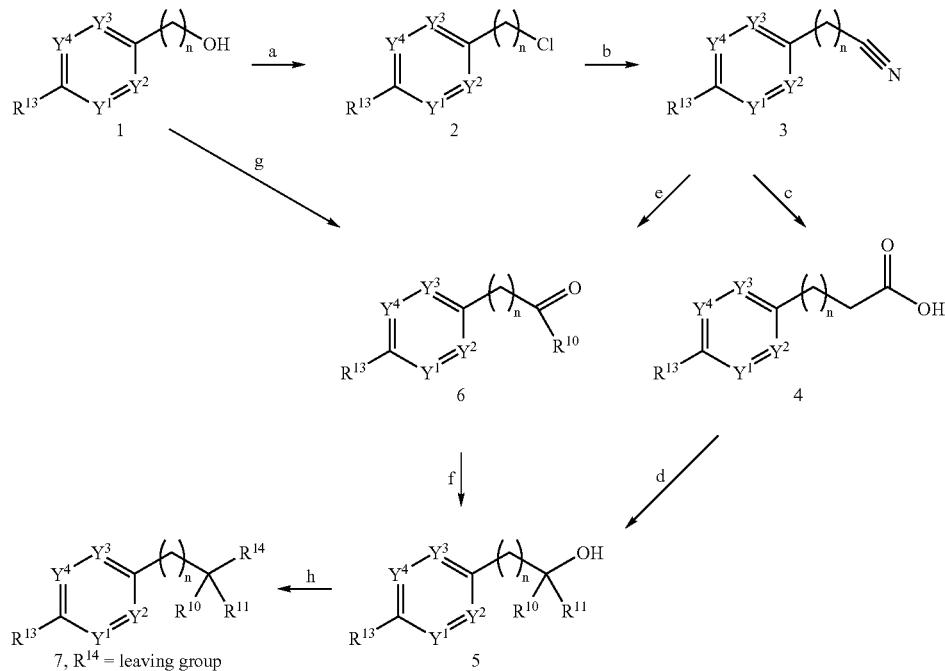

Alcohols 1 in scheme 9 comprising a chain length n equal to one or two can be converted into analogues with a chain length of n+1 carbon atoms by methods well known in the art, e.g. by conversion of the primary alcohol into a suitable leaving group, e.g. a halide (2, step a), followed by reaction with cyanide to form nitriles 3 (step b) and saponification to acids 4 (step c). Acids 4 can be further transformed into the primary alcohols 5 ($R^{10}$=H, $R^{11}$=H), e.g. by using diborane in tetrahydrofuran (step d). Optionally, such alcohols 5 can be elongated to a chain length of n+1 carbon atoms by repeating the synthesis described for alcohols 1 to 5. In order to introduce substituents $R^{10}$ and/or $R^{11}$ different from hydrogen, cyano intermediates 3 can be reacted with alkyl Grignard reagents $R^{10}$MgX in solvents like ether or tetrahydrofuran between 0° C. and then reflux temperature of the solvent to form the corresponding $R^{10}$CO-alkyl ketones 6 (step e) or with diisbutylaluminium hydride the corresponding aldehydes 6 ($R^{10}$=H). Treatment of compounds 6 with an alkyllithium reagent $R^{11}$Li in solvents like ether or tetrahydrofuran gives alcohols 5 (step f); treatment of compounds 6 with lithium aluminium hydride in solvents like tetrahydrofuran or ether or with sodium borohydride in solvents like ethanol or methanol, preferably at temperatures between −15° C. and 40° C., gives alcohols 5 with $R^{11}$=H (step f). The alcohol compounds 5 which contain a chiral center can optionally be separated into optically pure antipodes by methods well known in the art, e.g. chromatography on a chiral HPLC column, or by derivatization with an optically pure acid to form esters, which can be separated by conventional HPLC chromatography and can then be converted back to the enantiomericaly pure alcohols 5. The reduction of ketones 6 to the corresponding secondary alcohols 5 of scheme 9 can also be carried out in an enantioselective fashion leading to the (R)- or (S)-alcohols 5, e.g. by treatment with borane-dimethylsulfide complex and (S)- or (R)-2-methyl-CBS-oxazaborolidine as chiral catalyst in tetrahydrofuran, preferably at temperatures between −78° C. and ambient temperature, according to Corey et al. (E. J. Corey, R. K. Bakshi, S. Shibata, *J. Am. Chem. Soc.* 1987, 109, 5551-5553), or by treatment with (+)- or (−)-B-chlorodiisopinocampheyl-borane (DIP-Cl), according to Brown et al. (P. V. Ramachandran, B. Gong, A. V. Teodorovic, H. C. Brown, *Tetrahedron: Asymmetry* 1994, 5, 1061-1074). Aldehydes 6 ($R^{10}$=H, n=0) can also be synthesized from primary alcohols 1 by methods known in the art, e.g. by treatment with pyridinium chlorochromate in dichloromethane, preferably at temperatures between room temperature and the reflux temperature of dichloromethane, or by treatment with manganese dioxide in solvents like dichloromethane, preferably at room temperature (step g). These aldehydes 6 can be converted to the corresponding secondary alcohols 5 through reaction with alkyl organometallic compounds, preferably under the conditions discussed above. Finally, the alcohols 5 of scheme 9 can be converted into compounds of formula 7, e.g by treatment with methanesulfonyl chloride in dichloromethane in the presence of a base like triethylamine preferably in a temperature range between −20° C. and room temperature or thionyl chloride in dichloromethane at 0° C. to room temperature or by reaction with carbon tetrachloride or carbon tetrabromide and triphenylphosphine in solvents like tetrahydrofuran preferably in a temperature range between room temperature and the reflux temperature of the solvents or by treatment with triflic anhydride, 2,6-lutidine and 4-dimethylaminopyridine in dichloromethane between −30° C. and room temperature; thus yielding compounds of formula 7 as methane-sulfonates, triflates, chlorides or bromides, respectively (step h).

The following tests were carried out in order to determine the activity of the compounds of formula (I).

Background information on the performed assays can be found in: Nichols J S et al. "Development of a scintillation proximity assay for peroxisome proliferator-activated receptor gamma ligand binding domain", (1998) Anal. Biochem. 257:112-119.

Full-length cDNA clones for humans PPARδ and PPARα and mouse PPARγ were obtained by RT-PCR from human adipose and mouse liver cRNA, respectively, cloned into plasmid vectors and verified by DNA sequencing. Bacterial and mammalian expression vectors were constructed to produce glutathione-s-transferase (GST) and Gal4 DNA binding domain proteins fused to the ligand binding domains (LBD) of PPARδ (aa 139 to 442), PPARγ (aa 174 to 476) and PPARα (aa 167 to 469). To accomplish this, the portions of the cloned sequences encoding the LBDs were amplified from the full-length clones by PCR and then subcloned into the plasmid vectors. Final clones were verified by DNA sequence analysis.

Induction, expression, and purification of GST-LBD fusion proteins were performed in *E. coli* strain BL21 (pLysS) cells by standard methods (Ref: Current Protocols in Molecular Biology, Wiley Press, edited by Ausubel et al.).

Radioligand Binding Assay

PPARδ receptor binding was assayed in HNM10 (50 mM Hepes, pH 7.4, 10 mM NaCl, 5 mM $MgCl_2$, 0.15 mg/ml fatty acid-free BSA and 15 mM DTT). For each 96 well reaction a 500 ng equivalent of GST-PPARδ-LBD fusion protein and radioligand, e.g. 20000 dpm {2-methyl-4-[4-methyl-2-(4-trifluoromethyl-phenyl)-thiazol-5-yl-ditritiomethylsulfanyl]-phenoxy}-acetic acid, was bound to 10 µg SPA beads (PharmaciaAmersham) in a final volume of 50 µl by shaking. The resulting slurry was incubated for 1 h at RT and centrifuged for 2 min at 1300 g. The supernatant containing unbound protein was removed and the semidry pellet containing the receptor-coated beads was resuspended in 50 µl of HNM. Radioligand was added and the reaction incubated at RT for 1 h and scintillation proximity counting performed in the presence of test compounds was determined. All binding assays were performed in 96 well plates and the amount of bound ligand was measured on a Packard TopCount using Opti-Plates (Packard). Dose response curves were done in triplicates within a range of concentration from $10^{-10}$ M to $10^{-4}$ M.

PPARα receptor binding was assayed in TKE50 (50 mM Tris-HCl, pH 8, 50 mM KCl, 2 mM EDTA, 0.1 mg/ml fatty acid-free BSA and 10 mM DTT). For each 96 well reaction an 140 ng equivalent of GST-PPARα-LBD fusion protein was bound to 10 µg SPA beads (PharmaciaAmersham) in a final volume of 50 µl by shaking. The resulting slurry was incubated for 1 h at RT and centrifuged for 2 min at 1300 g. The supernatant containing unbound protein was removed and the semidry pellet containing the receptor-coated beads was resolved in 50 µl of TKE. For radioligand binding e.g. 10000 dpm of 2(S)-(2-benzoyl-phenylamino)-3-{4-[1,1-ditritio-2-(5-methyl-2-phenyl-oxazol-4-yl)-ethoxy]-phenyl}-propionic acid or 2,3-ditritio-2(S)-methoxy-3-{4-[2-(5-methyl-2-phenyl-oxazol-4-yl)-ethoxy]-benzo[b]thiophen-7-yl}-propionic acid in 50 µl were added, the reaction incubated at RT for 1 h and scintillation proximity counting performed. All binding assays were performed in 96 well plates and the amount of bound ligand measured on a Packard TopCount using OptiPlates (Packard). Nonspecific binding was determined in the presence of $10^{-4}$ M unlabelled compound. Dose response curves were done in triplicates within a range of concentration from $10^{-10}$ M to $10^{-4}$ M.

PPARγ receptor binding was assayed in TKE50 (50 mM Tris-HCl, pH 8, 50 mM KCl, 2 mM EDTA, 0.1 mg/ml fatty acid-free BSA and 10 mM DTT). For each 96 well reaction an 140 ng equivalent of GST-PPARγ-LBD fusion protein was bound to 10 µg SPA beads (PharmaciaAmersham) in a final volume of 50 ul by shaking. The resulting slurry was incubated for 1 h at RT and centrifuged for 2 min at 1300 g. The supernatant containing unbound protein was removed and the semidry pellet containing the receptor-coated beads was resolved in 50 ul of TKE. For radioligand binding e.g. 10000 dpm 2(S)-(2-benzoyl-phenylamino)-3-{4-[1,1-ditritio-2-(5-methyl-2-phenyl-oxazol-4-yl)-ethoxy]-phenyl}-propionic acid in 50 µl were added, the reaction incubated at RT for 1 h and scintillation proximity counting performed. All binding assays were performed in 96 well plates and the amount of bound ligand measured on a Packard TopCount using OptiPlates (Packard). Nonspecific binding was determined in the presence of $10^{-4}$ M unlabelled compound. Dose response curves were done in triplicates within a range of concentration from $10^{-10}$ M to $10^{-4}$ M.

Luciferase Transcriptional Reporter Gene Assays

Baby hamster kidney cells (BHK21 ATCC CCL10) were grown in DMEM medium containing 10% FBS at 37° C. in a 95% O2:5% $CO_2$ atmosphere. Cells were seeded in 6 well plates at a density of $10^5$ Cells/well and then batch-transfected with either the pFA-PPARδ-LBD, pFA-PPARγ-LBD or pFA-PPARα-LBD expression plasmids plus a reporter plasmid. Transfection was accomplished with the Fugene 6 reagent (Roche Molecular Biochemicals) according to the suggested protocol. Six hours following transfection, the cells were harvested by trypsinization and seeded in 96 well plates at a density of $10^4$ cells/well. After 24 hours to allow attachment of cells, the medium was removed and replaced with 100 ul of phenol red-free medium containing the test substances or control ligands (final DMSO concentration: 0.1%). Following incubation of the cells for 24 hours with substances, 50 µl of the supernatant was was discarded and then 50 µl of Luciferase Constant-Light Reagent (Roche Molecular Biochemicals) to lyse the cells and initiate the luciferase reaction was added. Luminescence for luciferase was measured in a Packard TopCount. Transcriptional activation in the presence of a test substance was expressed as fold-activation over cells incubated in the absence of the substance. EC50 values were calculated using the XLfit program (ID Business Solutions Ltd. UK).

The free acids of the compounds of the present invention ($R^1$ is hydrogen) exhibit $IC_{50}$ values of 0.5 nM to 10 µM, preferably 1 nM to 100 nM for PPARδ and $IC_{50}$ values of 1 nM to 10 µM, preferably 10 nM to 5 µM for PPARα. Compounds, in which $R^1$ is not hydrogen are converted in vivo to compounds in which $R^1$ is hydrogen. The following table shows measured values for some selected compounds of the present invention.

|  | PPARα $IC_{50}$ (µmol/l) | PPARγ $IC_{50}$ (µmol/l) | PPARδ $IC_{50}$ (µmol/l) |
|---|---|---|---|
| Example 3 | 3.58 | >10 | 0.065 |
| Example 4 | 0.037 | >10 | 0.295 |
| Example 5 | 0.716 | >10 | 0.106 |

The compounds of formula (I) and their pharmaceutically acceptable salts and esters can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula (I) and their pharmaceutically acceptable, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 1 mg to about 100 mg, comes into consideration. Depending on the dosage it is convenient to administer the daily dosage in several dosage units.

The pharmaceutical preparations conveniently contain about 0.1-500 mg, preferably 0.5-100 mg, of a compound of formula (I).

The following examples serve to illustrate the present invention in more detail. They are, however, not intended to limit its scope in any manner.

EXAMPLES

Abbreviations:
AcOEt=ethyl acetate, n-BuLi=n-butyllithium, DBU=1,8-diazabicyclo[5.4.0]undec-7-ene, DEAD=diethyl azodicarboxylate, DIAD=diisopropyl azodicarboxylate, DIBAL-H=diisobutylaluminum hydride, DMF=N,N-dimethylformamide, DMPU=1,3-dimethyl-3,4,5,6-tetrahydro-2(1H)-pyrimidinone, eq.=equivalents, h=hour(s), DMSO=dimethyl sulfoxide, HPLC=high performance liquid chromatography, i. V.=in vacuo, LDA=lithium diisopropylamide, POCl$_3$=phosphorous oxychloride, RT=room temperature, TFA=trifluoroacetic acid, THF=tetrahydrofuran.

Example 1

[rac]-[4-(Methyl-{1-[2-methyl-6-(4-trifluoromethyl-phenyl)-pyridin-3-yl]-ethyl}-amino)-naphthalen-1-yloxy]-acetic acid A] (4-Hydroxy-naphthalen-1-yl)-carbamic acid tert-butyl ester 3.00 g (18.47 mmol) of commercially available 4-amino-naphthalen-1-ol hydrochloride was suspended in 19 ml of abs. THF and treated successively at 0° C. with 2.70 ml (19.4 mmol) of triethylamine and 4.837 g (22.2 mmol) of di-tert-butyl dicarbonate. The reaction was then allowed to proceed for 1 h at 80° C. After cooling, the mixture was poured onto crashed ice/NH$_4$Cl, extracted twice with AcOEt, washed with water and brine, and dried over sodium sulfate. Evaporation of the solvents, followed by crystallization from hexane/AcOEt afforded 3.337 g of the title compound as reddish crystals of mp. 182-183° C.

MS: 258.0 (M−H)$^−$.

B] (4-tert-Butoxycarbonylamino-naphthalen-1-yloxy)-acetic acid ethyl ester 3.33 g (12.8 mmol) of 4-hydroxy-naphthalen-1-yl-carbamic acid tert-butyl ester was dissolved in 60 ml of acetone and treated at 0° C. subsequently with 4.60 g (1.1 eq.) of cesium carbonate, 0.107 g (0.05 eq.) of KI, and 1.42 ml (1.0 eq.) of ethyl bromoacetate. After vigorous stirring for 1 h at ambient temperature, the solvent was evaporated and the residue redissolved in AcOEt. Washing with water, drying over magnesium sulfate, and evaporation of the solvents, followed by flash chromatography (SiO$_2$, hexane/AcOEt=75/25), yielded 4.28 g of the title product as off-white crystals.

MS: 346.2 (M+H)$^+$, 363.3 (M+NH$_4$)$^+$.

C] [4-(tert-Butoxycarbonyl-methyl-amino)-naphthalen-1-yloxy]-acetic acid ethyl ester To 4.28 g (12.4 mmol) of the above prepared 4-tert-butoxycarbonylamino-naphthalen-1-yloxy)-acetic acid ethyl ester, dissolved in 37 ml of abs. DMF, was added at 0° C. 0.644 g of NaH (60% in mineral oil, 1.3 eq.). 5 Min. later, 1.55 ml (2 eq.) of MeI was added and the reaction allowed to proceed for 10 Min. at 0° C. and for 1 h at ambient temperature. Pouring onto crashed ice/KHSO$_4$, twofold extraction with AcOEt, washing with water and brine, drying over magnesium sulfate, and evaporation of the solvents, followed by flash chromatography (SiO$_2$, hexane/AcOEt=8/2), yielded 3.90 g of the title compound as colorless oil.

D] (4-Methylamino-naphthalen-1-yloxy)-acetic acid ethyl ester

To 3.90 g (10.9 mmol) of the above prepared [4-(tert-butoxycarbonyl-methyl-amino)-naphthalen-1-yloxy]-acetic acid ethyl ester, dissolved in 110 ml of CH$_2$Cl$_2$, was added via dropping funnel within 15 Min. 27.9 ml of TFA. After additional 30 Min. at RT, the bulk of the solvents was removed i. V. and the residue distributed between NaHCO$_3$ and AcOEt. Washing with cold water and brine, drying over magnesium sulfate, and evaporation of the solvents, followed by flash chromatography (SiO$_2$, hexane/AcOEt=8/2), gave 2.25 g of the title compound as off-white crystals.

MS: 260.2 (M+H)$^+$.

E] [rac]-[4-(Methyl-{1-[2-methyl-6-(4-trifluoromethyl-phenyl)-pyridin-3-yl]-ethyl}-amino)-naphthalen-1-yloxy]-acetic acid ethyl ester 0.095 g (0.37 mmol) of the above prepared (4-methylamino-naphthalen-1-yloxy)-acetic acid ethyl ester and 0.220 g of [rac]-3-(1-chloro-ethyl)-2-methyl-6-(4-trifluoromethyl-phenyl)-pyridine (see below 1G], 2.0 eq.) were treated in 2.8 ml of DMSO with 0.110 g (1 eq.) of NaI and 0.168 g (1.5 eq.) of DBU. After stirring for 20 h at 40° C., the reaction mixture was poured onto crashed ice/KHSO$_4$, extracted twice with AcOEt, washed with water and brine, and dried over sodium sulfate. Evaporation of the solvents, followed by flash chromatography (SiO$_2$, hexane/AcOEt=85/15), afforded 0.055 g of the title compound as light brown oil.
MS: 523.5 (M+H)$^+$.

F] [rac]-[4-(Methyl-{1-[2-methyl-6-(4-trifluoromethyl-phenyl)-pyridin-3-yl]-ethyl}-amino)-naphthalen-1-yloxy]-acetic acid 0.055 g (0.11 mmol) of the above prepared [rac]-[4-(methyl-{1-[2-methyl-6-(4-trifluoromethyl-phenyl)-pyridin-3-yl]-ethyl}-amino)-naphthalen-1-yloxy]-acetic acid ethyl ester was dissolved in 0:6 ml of THF/EtOH=1/1, treated with 0.33 ml (3 eq.) of 1N NaOH, and kept at 0° C. for 2 h. The reaction mixture was then poured onto crashed ice/AcOEt/HCl dil., the organic layer washed with water and brine, dried over sodium sulfate, and evaporated to dryness. Crystallization from hexane/AcOEt afforded finally 0.040 g of the title compound as off-white solid of mp. 157-58° C.
MS: 493.1 (M−H)$^−$.

The reagent used in 1E] was synthesized as follows:

G] 3-Dimethylamino-1-(4-trifluoromethyl-phenyl)-propan-1-one hydrochloride 4-(Trifluoromethyl) acetophenone (4.97 g, 26.4 mmol), paraformaldehyde (1.586 g, 2 eq.), dimethylamine hydrochloride (3.231 g, 1.5 eq.) were mixed together in 7 ml of EtOH, treated with 0.08 ml of 37% HCl, and heated to reflux for 5 h. Cooling down to ambient temperature, filtration and washing with tiny amounts of cold EtOH delivered 4.59 g of the title compound as white crystals of mp. 128-142° C. (dec.).
MS: 246.3 (M+H)$^+$.

H] 2-Methyl-6-(4-trifluoromethyl-phenyl)-nicotinic acid methyl ester 4.59 g (16.3 mmol) of the above prepared 3-dimethylamino-1-(4-trifluoromethyl-phenyl)-propan-1-one hydrochloride and 1.86 g (1.00 eq.) of 3-aminocrotonic acid methyl ester were dissolved in 50 ml of AcOH and heated to reflux for 4 h. After cooling, the bulk of the solvent was evaporated i. V., the residue dissolved in AcOEt, and washed with water and brine. Drying over sodium sulfate, evaporation of the solvents and flash chromatography (SiO$_2$, hexane/AcOEt=8/2) delivered finally 2.40 g of the title compound as light yellow waxy solid.
MS: 296.1 (M+H)$^+$.

I] [2-Methyl-6-(4-trifluoromethyl-phenyl)-pyridin-3-yl]-methanol 1.00 g (3.39 mmol) of the above synthesized 2-methyl-6-(4-trifluoromethyl-phenyl)-nicotinic acid methyl ester in 7 ml of abs. THF was cooled down to 0° C. and reacted with 7.06 ml of DIBAL-H-solution (1.2 M in toluene, 2.5 eq.) for 1 h. Careful quenching with ice/NH$_4$Cl, twofold extraction with AcOEt, washing with brine, drying over sodium sulfate, and evaporation of the solvents left a crude product which was purified by flash chromatography (SiO$_2$, hexane/AcOEt=7/3) to deliver finally 0.875 g of the title compound as off-white solid of mp. 76-78° C.
MS: 268.1 (M+H)$^+$.

J] 2-Methyl-6-(4-trifluoromethyl-phenyl)-pyridine-3-carbaldehyde 1.00 g (3.74 mmol) of the above prepared [2-methyl-6-(4-trifluoromethyl-phenyl)-pyridin-3-yl]-methanol was dissolved in 19 ml of CH$_2$Cl$_2$ and treated with 3.253 g (10 eq.) of MnO$_2$. After vigorous stirring for 4 h at ambient temperature, the reaction mixture was filtered over Celite and carefully rinsed with CH$_2$Cl$_2$. Evaporation of the solvent left 0.920 g of the title compound, pure according to NMR and used as such for the next step.
MS: 266.2 (M+H)$^+$.

K] [rac]-1-[2-Methyl-6-(4-trifluoromethyl-phenyl)-pyridin-3-yl]-ethanol 0.470 g (1.77 mmol) of the above prepared 2-methyl-6-(4-trifluoromethyl-phenyl)-pyridine-3-carbaldehyde was dissolved in 9 ml of abs. THF and treated at −10° C. with 0.89 ml of 3M methyl magnesium chloride solution (in THF). After 15 Min., the reaction mixture was carefully poured onto crashed ice/NH$_4$Cl, extracted twice with AcOEt, washed with water and brine, dried over sodium sulfate, and evaporated to dryness to leave 0.508 g of the title product, pure according to NMR.
MS: 282.2 (M+H)$^+$.

L] [rac]-3-(1-Chloro-ethyl)-2-methyl-6-(4-trifluoromethyl-phenyl)-pyridine 0.472 g (1.68 mmol) of the above prepared [rac]-1-[2-methyl-6-(4-trifluoromethyl-phenyl)-pyridin-3-yl]-ethanol was dissolved in 8 ml of CH$_2$Cl$_2$ and treated dropwise at 0° C. with 0.399 ml (2 eq.) of SOCl$_2$. The reaction mixture was kept at 0° for 5 Min. and at RT for 30 Min. Pouring onto crashed ice/NaHCO$_3$, twofold extraction with AcOEt, washing with water, drying over sodium sulfate, and evaporation of the solvents yielded 0.488 g of pure title compound as light yellow oil.
MS: 299.1, 301.1 (M)$^+$.

Example 2

[rac]-[4-(Methyl-{1-[2-methyl-6-(3-trifluoromethyl-phenyl)-pyridin-3-yl]-propyl}-amino)-naphthalen-1-yloxy]-acetic acid

A] [rac]-[4-(Methyl-{1-[2-methyl-6-(3-trifluoromethyl-phenyl)-pyridin-3-yl]-propyl}-amino)-naphthalen-1-yloxy]-acetic acid ethyl ester To 0.164 g (0.523 mmol) of [rac]-3-(1-chloro-propyl)-2-methyl-6-(3-trifluoromethyl-phenyl)-pyridine (see below 2C]) and 0.149 g (0.575 mmol) of the above prepared (4-methylamino-naphthalen-1-yloxy)-acetic acid ethyl ester, dissolved in 3.2 ml of abs. DMSO, were added successively 0.0867 g of K$_2$CO$_3$ (0.627 mmol) and 0.0856 g (0.575 mmol)

of NaI. The reaction was allowed to proceed for 15 h at 60° C. Pouring onto crashed ice/NH$_4$Cl, twofold extraction with AcOEt, washing with water, drying over sodium sulfate, and evaporation of the solvents, followed by flash chromatography (SiO$_2$, hexane/AcOEt=9/1), yielded 0.043 g of the title compound as light yellow oil.
MS: 537.6 (M+H)$^+$.

B] [rac]-[4-(Methyl-{1-[2-methyl-6-(3-trifluoromethyl-phenyl)-pyridin-3-yl]-propyl}-amino)-naphthalen-1-yloxy]-acetic acid 0.042 g (0.078 mmol) of the above prepared [rac]-[4-(methyl-{1-[2-methyl-6-(3-trifluoromethyl-phenyl)-pyridin-3-yl]-propyl}-amino)-naphthalen-1-yloxy]-acetic acid ethyl ester was dissolved in 0.84 ml of THF/EtOH=1/1, treated at 0° C. with 0.24 ml (3 eq.) of 1N NaOH, and kept at ambient temperature for 2 h. The reaction mixture was then neutralized with HCl dil. to pH 7, extracted with AcOEt, the organic layer was washed with water, dried over sodium sulfate, and evaporated to dryness to leave, after crystallization from AcOEt/hekane, 0.033 g of the title compound as yellowish crystals of mp. 76-78° C.
MS: 509.6 (M+H)$^+$.

The necessary reagent was prepared as follows:

C] 3-Dimethylamino-1-(3-trifluoromethyl-phenyl)-propan-1-one hydrochloride 3-(Trifluoromethyl) acetophenone (5.00 g, 26.6 mmol), paraformaldehyde (1.596 g, 2 eq.), dimethylamine hydrochloride (3.25 g, 1.5 eq.) were mixed together in 7 ml of EtOH, treated with 0.08 ml of 37% HCl, and heated to reflux for 5 h. Cooling down to ambient temperature, filtration and washing with tiny amounts of cold EtOH delivered 5.58 g of the title compound as white crystals of mp. 144-146° C. (dec.).
MS: 246.2 (M+H)$^+$.

D] 2-Methyl-6-(3-trifluoromethyl-phenyl)-nicotinic acid methyl ester 5.57 g (19.76 mmol) of the above prepared 3-dimethylamino-1-(3-trifluoromethyl-phenyl)-propan-1-one hydrochloride and 2.28 g (1.00 eq.) of 3-aminocrotonic acid methyl ester were dissolved in 60 ml of AcOH and heated to reflux for 4 h. After cooling, the bulk of the solvent was evaporated i. V., the residue dissolved in AcOEt and washed with water and brine. Drying over sodium sulfate, evaporation of the solvents and flash chromatography (SiO$_2$, hexane/AcOEt=89/11) delivered finally 2.00 g of the title compound as light yellow crystals of mp. 47-49° C. (dec.).
MS: 295.1 (M)$^+$.

E] [2-Methyl-6-(3-trifluoromethyl-phenyl)-pyridin-3-yl]-methanol 1.96 g (6.62 mmol) of the above synthesized 2-methyl-6-(3-trifluoromethyl-phenyl)-nicotinic acid methyl ester in 14 ml of abs. THF was cooled down to 0° C. and reacted with 13.8 ml of DIBAL-H-solution (1.2 M in toluene, 2.5 eq.) for 1 h. Careful quenching with ice/NH$_4$Cl, twofold extraction with AcOEt, washing with brine, drying over sodium sulfate, and evaporation of the solvents left a crude product which was purified by flash chromatography (SiO$_2$, hexane/AcOEt=55/45) to deliver finally 1.66 g of the title compound as white crystals of mp. 75-77° C.
MS: 268.1 (M+H)$^+$.

F] 2-Methyl-6-(3-trifluoromethyl-phenyl)-pyridine-3-carbaldehyde 3.00 g (11.2 mmol) of the above prepared [2-methyl-6-(3-trifluoromethyl-phenyl)-pyridin-3-yl]-methanol was dissolved in 56 ml of CH$_2$Cl$_2$ and treated with 14.6 g (15 eq.) of MnO$_2$. After vigorous stirring for 2 h at ambient temperature, the reaction mixture was filtered over Celite and carefully rinsed with CH$_2$Cl$_2$. Evaporation of the solvent left 2.659 g of the title compound as white crystals of mp. 61-63° C.
MS: 266.0 (M+H)$^+$.

G] [rac]-1-[2-Methyl-6-(3-trifluoromethyl-phenyl)-pyridin-3-yl]-propan-1-ol 0.600 g (2.26 mmol) of the above prepared 2-methyl-6-(3-trifluoromethyl-phenyl)-pyridine-3-carbaldehyde was dissolved in 11 ml of abs. THF and treated at −15° C. with 1.08 ml of 2.5 M ethyl magnesium chloride solution (in THF). After 30 Min., the reaction mixture was carefully poured onto crashed ice/NH$_4$Cl, extracted twice with AcOEt, washed with water and brine, dried over sodium sulfate, and evaporated to dryness. Flash chromatography (SiO$_2$, hexane/AcOEt=8/2) produced finally 0.473 g of pure title compound as white crystals of mp. 97-99° C.
MS: 266.0 (M+H)$^+$.

H] [rac]-3-(1-Chloro-propyl)-2-methyl-6-(3-trifluoromethyl-phenyl)-pyridine 0.468 g (1.58 mmol) of the above prepared [rac]-1-[2-methyl-6-(3-trifluoromethyl-phenyl)-pyridin-3-yl]-propan-1-ol was dissolved in 7.6 ml of CH$_2$Cl$_2$ and treated dropwise at 0° C. with 0.23 ml (2 eq.) of SOCl$_2$. The reaction mixture was kept at 0° C. for 5 Min. and at RT for 30 Min. Pouring onto crashed ice/NaHCO$_3$, twofold extraction with AcOEt, washing with water, drying over sodium sulfate, and evaporation of the solvents yielded 0.496 g of pure title compound as light yellow oil.
MS: 314.1, 316.1 (M+H)$^+$.

Example 3

A] [rac]-[4-(Methyl-{1-[2-methyl-6-(3-trifluoromethyl-phenyl)-pyridin-3-yl]-butyl}-amino)-naphthalen-1-yloxy]-acetic acid The title compound was prepared in analogy to example 2, but using in step A] [rac]-3-(1-chloro-butyl)-2-methyl-6-(3-trifluoromethyl-phenyl)-pyridine instead of [rac]-3-(1-chloro-propyl)-2-methyl-6-(3-trifluoromethyl-phenyl)-pyridine, as yellow foam.
MS: 521.2 (M−H)$^−$.

The necessary reagent

B] [rac]-3-(1-chloro-butyl)-2-methyl-6-(3-trifluoromethyl-phenyl)-pyridine was prepared in analogy to example 2G]-H], but using propylmagnesium chloride instead of ethylmagnesium chloride, as yellow oil.
MS: 327.2, 329.2 (M)$^+$.

Example 4

[rac]-2-Methoxy-3-(4-{2-[2-methyl-6-(4-trifluoromethyl-phenyl)-pyridin-3-yl]-ethoxy}-naphthalen-2-yl)-propionic acid

A] 4-Benzyloxy-naphthalene-2-carbaldehyde 4.00 g (15.1 mmol) of (4-benzyloxy-naphthalen-2-yl)-methanol [PCT Int. Appl. (1997), WO 97/09311A1] was dissolved in 160 ml of EtOAc; then, 54.1 g of manganese dioxide was added in small portions and the reaction mixture was stirred for 30 Min. at ambient temperature. The dark suspension was filtered with the aid of dicalite; then, the solvent was evaporated. Flash chromatography ($SiO_2$, hexane/EtOAc=4:1) gave 3.20 g of the title compound as colorless oil.
MS: 262.2 $(M)^+$.

B] 3-(4-Benzyloxy-naphthalen-2-yl)-2-methoxy-(Z,E)-acrylic acid methyl ester To a solution of 22.92 g (57.2 mmol) of (1,2-dimethoxy-2-oxoethyl)triphenyl phosphonium chloride (example 4F]) in 140 ml of $CH_2Cl_2$ was added 7.87 ml (61 mmol) of tetramethyl guanidine at 0° C. and the mixture was warmed up to ambient temperature. The reaction mixture was then treated with 5.00 g (19.1 mmol) of the above prepared 4-benzyloxy-naphthalene-2-carbaldehyde and stirred for 22 hours at 40° C. It was then evaporated and the residue partitioned between AcOEt and water/HCl. The organic layer was washed with water, dried over magnesium sulfate, filtered and evaporated. The residue was chromatographed on $SiO_2$ (n-hexane/AcOEt=98:2 to 95:5) to give 5.70 g of the title compound as colorless solid.
MS: 348.1 $(M)^+$.

C] [rac]-3-(4-Hydroxy-naphthalen-2-yl)-2-methoxy-propionic acid methyl ester 5.70 g (16.4 mmol) of the above prepared 3-(4-benzyloxy-naphthalen-2-yl)-2-methoxy-(Z,E)-acrylic acid methyl ester was dissolved in 90 ml of THF; 1.15 g of Pd—C (10%) was added and the reaction mixture hydrogenated at ambient temperature and atmospheric pressure for two hours. It was subsequently filtered with the aid of dicalite and evaporated. Flash chromatography ($SiO_2$, hexane/EtOAc=4:1) gave 3.95 g of the title compound as yellow oil.
MS: 259.1 $(M–H)^-$.

D] [rac]-2-Methoxy-3-(4-{2-[2-methyl-6-(4-trifluoromethyl-phenyl)-pyridin-3-yl]-ethoxy}-naphthalen-2-yl)-propionic acid methyl ester 0.26 g (1.0 mmol) of the above prepared [rac]-3-(4-hydroxy-naphthalen-2-yl)-2-methoxy-propionic acid methyl ester, 0.30 g (1.05 mmol) of 2-[2-methyl-6-(4-trifluoromethyl-phenyl)-pyridin-3-yl]-ethanol (see below example 4K]) and 0.31 g (1.20 mmol) of triphenylphosphine were dissolved in 10 ml of THF. The stirred reaction mixture was cooled down to 0° C. and a solution of 0.27 g (1.15 mmol) of di-tert.-butyl azodicarboxylate in 5 ml of THF was added drop by drop and the reaction warmed up to ambient temperature. After 20 hours, the solvent was evaporated and the residue purified by chromatography ($SiO_2$, heptane/EtOAc=9:1 to 1:1) to give 0.45 g of the title compound as light yellow oil.
MS: 524.4 $(M+H)^+$.

E] [rac]-2-Methoxy-3-(4-{2-[2-methyl-6-(4-trifluoromethyl-phenyl)-pyridin-3-yl]-ethoxy}-naphthalen-2-yl)-propionic acid 0.43 g (0.82 mmol) of the above prepared [rac]-2-methoxy-3-(4-{2-[2-methyl-6-(4-trifluoromethyl-phenyl)-pyridin-3-yl]-ethoxy}-naphthalen-2-yl)-propionic acid methyl ester was dissolved in 15 ml of THF/MeOH (2:1); to the stirred solution was then added 1.64 ml of LiOH-solution (1 molar in water). After one hour, the reaction mixture was poured onto crashed ice/HCl and extracted twice with $CH_2Cl_2$; the organic layers were washed with water, dried over magnesium sulfate, filtered and evaporated. The residue was purified by chromatography [$SiO_2$, $CH_2Cl_2$/MeOH (0 to 5% MeOH)] to give 0.42 g of pure title compound as light yellow solid.
MS: 508.3 $(M–H)^-$.

(1,2-Dimethoxy-2-oxoethyl)triphenyl phosphonium chloride used in procedure 4B] has been prepared as follows:

F] (1,2-Dimethoxy-2-oxoethyl)triphenyl phosphonium chloride 0.45 g (3.5 mmol) of iodine was added to 105 ml (1.48 mol) of acetylchloride; then, 165.4 g (1.23 mol) of 2,2-dimethoxy-acetic acid methyl ester was added within 20 minutes below 30° C. and stirring was continued at room temperature for 1 hour and at 50° C. for 25 minutes. Subsequently, the reaction mixture was evaporated at 48° C./280 mbar giving 236.69 g of crude 2-chloro-2-methoxy-acetic acid methyl ester. The crude 2-chloro-2-methoxy-acetic acid methyl ester was then added within 15 minutes to a solution of 323.2 mg (1.23 mol) of triphenylphosphine, dissolved in 500 ml dichloromethane, while the temperature was kept between 16° C. and 26° C.

The reaction was subsequently stirred at room temperature for 20 hours, evaporated at 45° C./250 mbar, and the residue crystallized from dichloromethane/ethyl acetate giving 400.7 g of (1,2-dimethoxy-2-oxoethyl)triphenyl phosphonium chloride as colorless solid; microanalysis $C_{22}H_{22}ClO_3P$: C 65.80% found; C 65.92% calc.; H 5.40% found; H 5.53% calc.; P 7.82% found; 7.73% calc.; Cl 8.82% found; Cl 8.84% calc. [values corrected for 0.38% water found in the sample].

2-[2-Methyl-6-(4-trifluoromethyl-phenyl)-pyridin-3-yl]-ethanol used in procedure 4D] has been prepared as follows:

G] 3-Chloromethyl-2-methyl-6-(4-trifluoromethyl-phenyl)-pyridine

To a suspension of [2-methyl-6-(4-trifluoromethyl-phenyl)-pyridin-3-yl]-methanol (26.7 g; 100 mmol) (example 1I]) in dichloromethane (100 ml) was added at 0° C. 10.9 ml (150 mmol) of thionyl chloride within 0.5 hours. Stirring was continued at ambient temperature for 1 hour. Afterwards, ice water was added and the mixture was stirred vigorously. Then, the layers were separated, the aqueous phase was extracted with 100 ml of dichloromethane. The combined organic phases were washed with water, aqueous sodium hydrogen carbonate, brine, and dried over anhydrous sodium sulfate. After evaporation, 27.9 g of the title compound was obtained as light brown solid.
MS: 285.0 $(M)^+$.

H] [2-Methyl-6-(4-trifluoromethyl-phenyl)-pyridin-3-yl]-acetonitrile 27.2 g of the above prepared 3-chloromethyl-2-methyl-6-(4-trifluoromethyl-phenyl)-pyridine (95.2 mmol) was dissolved in 100 ml of dimethyl sulfoxide; 5.9 g of sodium cyanide (120 mmol) was added and the mixture was stirred at room temperature for 18 hours. Then, the reaction mixture was poured into a mixture of ice and water, and was subsequently extracted with 3 portions of 400 ml of tert-butyl methyl ether. The combined organic phases were washed with water, then with brine, and dried over anhydrous sodium sulfate. After evaporation of the solvent, 25.2 g of the title compound was obtained as pale yellow solid.

MS: 276.1 (M)$^+$.

I] [2-Methyl-6-(4-trifluoromethyl-phenyl)-pyridin-3-yl]-acetic acid

A mixture of 25 g (90 mmol) of the above prepared [2-methyl-6-(4-trifluoromethyl-phenyl)-pyridin-3-yl]-acetonitrile, 20 g of sodium hydroxide (500 mmol), 60 ml of water and 250 ml of propanol was stirred vigorously at 100° C. Hydrolysis was complete after 2 hours. The reaction mixture was then evaporated to dryness and the residue was dissolved in 70 ml of water; then, 60 ml of cold 8 N aqueous HCl was added and the acid was extracted with three portions of 250 ml of ethyl acetate; the combined organic phases were washed with water and brine, dried over anhydrous sodium sulfate, and evaporated to dryness. 25.1 g of the title product was obtained as pale yellow solid.

MS: 296.0 (M+H)$^+$.

J] [2-Methyl-6-(4-trifluoromethyl-phenyl)-pyridin-3-yl]-acetic acid methyl ester A solution of 2.55 g (8.63 mmol) of the above prepared [2-methyl-6-(4-trifluoromethyl-phenyl)-pyridin-3-yl]-acetic acid in 25 ml of methanol was cooled to −10° C.; 1.88 ml (25.9 mmol) of thionyl chloride was added. The reaction mixture was then stirred at ambient temperature for 2 hours. Subsequently, the solution was stirred with ice water, then extracted with three portions of 50 ml of tert.-butyl methyl ether. The combined organic layers were washed with water, aqueous sodium hydrogen carbonate and brine, and dried over anhydrous sodium sulfate. After evaporation of the solvent, 2.6 g of the title compound was obtained as light brown solid.

MS: 309.1(M)$^+$.

K] 2-[2-Methyl-6-(4-trifluoromethyl-phenyl)-pyridin-3-yl]-ethanol 2.6 g (8.40 mmol) of the above prepared [2-methyl-6-(4-trifluoromethyl-phenyl)-pyridin-3-yl]-acetic acid methyl ester in 15 ml of dry tetrahydrofuran was added under an argon atmosphere within 15 minutes to a stirred suspension of 0.38 g (10 mmol) of lithium aluminum hydride in 5 ml of tetrahydrofuran. The reaction was exothermic. Subsequently, the mixture was stirred at room temperature for 1 hour. Then, 1 ml of ethyl acetate was dropped to the reaction mixture, followed by water, drop after drop, under argon, with stirring and cooling until the gas evolution ceased. The reaction mixture was diluted with 50 ml of ethyl acetate, dried over anhydrous sodium sulfate, and filtered. The filtrate was evaporated i. V. and the residue was chromatographed on SiO$_2$ with a mixture of dichloromethane and tert.-butyl methyl ether (4:1 vol./vol.) as eluent. Thereby, 1.88 g of the title compound was obtained as white solid.

MS: 281.1 (M)$^+$.

Example 5

3-{4-[2-Methyl-6-(4-trifluoromethyl-phenyl)-pyridin-3-ylmethoxy]-5,6,7,8-tetrahydro-naphthalen-1-yl}-propionic acid A] (E)-3-(4-Benzyloxy-5,6,7,8-tetrahydro-naphthalen-1-yl)-acrylic acid ethyl ester To a cooled suspension (−10° C.) of 0.9 g (3.38 mmol) of 4-benzyloxy-5,6,7,8-tetrahydronaphthalene-1-carboxaldehyde [PCT Int. Appl. (2002), WO2002/092084A1] in 10 ml of absolute ethanol were added successively 0.75 ml (3.7 mmol) of triethyl phosphonoacetate and 0.255 g (3.7 mmol) of powdered sodium ethylate. Then, the mixture was stirred at ambient temperature for 1 hour. Subsequently, the reaction mixture was poured onto crushed ice/diluted hydrochloric acid and the product was extracted twice with tert.-butyl methyl ether; the organic phase was washed with brine and dried over anhydrous sodium sulfate, and finally evaporated leaving 1.15 g of the title compound as light brown solid.

MS: 336.2 (M)$^+$.

B] 3-(4-Hydroxy-5,6,7,8-tetrahydro-naphthalen-1-yl)-propionic acid ethyl ester 1.15 g (3.41 mmol) of the above prepared (E)-3-(4-benzyloxy-5,6,7,8-tetrahydro-naphthalen-1-yl)-acrylic acid ethyl ester was dissolved in 20 ml of tetrahydrofuran and hydrogenated over 0.3 g of 10% of palladium on charcoal as catalyst at ambient temperature and atmospheric pressure. Filtering off the catalyst and evaporating the solvent yielded 0.84 g of the title compound as grey solid.

MS: 248.2 (M)$^+$.

C] 3-{4-[2-Methyl-6-(4-trifluoromethyl-phenyl)-pyridin-3-ylmethoxy]-5,6,7,8-tetrahydro-naphthalen-1-yl}-propionic acid ethyl ester A mixture of 103 mg (0.41 mmol) of the above prepared 3-(4-hydroxy-5,6,7,8-tetrahydro-naphthalen-1-yl)-propionic acid ethyl ester, 118 mg (0.41 mmol) of 3-chloromethyl-2-methyl-6-(4-trifluoromethyl-phenyl)-pyridine (example 4G]) and 175 mg (0.54 mmol) of cesium carbonate in 5 ml of acetonitrile was stirred at 60° C. for 2 hours. Then, the solvent was evaporated i. V. and the residue was chromatographed on SiO$_2$ with a mixture of dichloromethane and tert.-butyl methyl ether (98:2, vol./vol.) as eluent. Thereby, 169 mg of the title compound was obtained as off white solid.

MS: 498.4 (M+H)$^+$.

D] 3-{4-[2-Methyl-6-(4-trifluoromethyl-phenyl)-pyridin-3-ylmethoxy]-5,6,7,8-tetrahydro-naphthalen-1-yl}-propionic acid 160 mg (0.32 mmol) of the above prepared 3-{4-[2-methyl-6-(4-trifluoromethyl-phenyl)-pyridin-3-ylmethoxy]-5,6,7,8-tetrahydro-naphthalen-1-yl}-propionic acid ethyl ester was dissolved in 5 ml of ethanol; 1.0 ml of 2N aqueous lithium hydroxide solution was added and the solution was heated to reflux for 1 hour. Then, the solution was cooled to room temperature and 1.0 ml of 2N aqueous hydrochloric acid was added. The white precipitated solid was filtered off, washed with water, and dried. 140 mg of the title product was thereby obtained as off-white solid.

MS: 468.3 (M−H)$^−$.

Example 6

3-{4-[2-Methyl-6-(4-trifluoromethyl-phenyl)-pyridin-3-ylmethoxy]-naphthalen-1-yl}-propionic acid In analogy to the procedures described in example 5C] and 5D], 3-(4-hydroxy-naphthalen-1-yl)-propionic acid ethyl ester [Helvetica Chimica Acta (2001), 84(8), 2198-2211] was reacted with 3-chloromethyl-2-methyl-6-(4-trifluoromethyl-phenyl)-pyridine (example 4G]) to give 3-{4-[2-methyl-6-(4-trifluoromethyl-phenyl)-pyridin-3-ylmethoxy]-naphthalen-1-yl}-propionic acid ethyl ester, which was subsequently saponified to yield the title compound as light pink solid.
MS: 464.2 (M−H)−.

Example 7

3-(4-{2-[2-Methyl-6-(4-trifluoromethyl-phenyl)-pyridin-3-yl]-ethoxy}-5,6,7,8-tetrahydro-naphthalen-1-yl)-propionic acid In analogy to the procedures described in example 4D] and 4E], 3-(4-hydroxy-5,6,7,8-tetrahydro-naphthalen-1-yl)-propionic acid ethyl ester (example 5B]) was reacted with 2-[2-methyl-6-(4-trifluoromethyl-phenyl)-pyridin-3-yl]-ethanol (example 4K]) to give 3-(4-{2-[2-methyl-6-(4-trifluoromethyl-phenyl)-pyridin-3-yl]-ethoxy}-5,6,7,8-tetrahydro-naphthalen-1-yl)-propionic acid ethyl ester, which was subsequently saponified to yield the title compound as colorless solid.
MS: 482.3 (M−H)−.

Example 8

3-(4-{2-[2-Methyl-6-(4-trifluoromethyl-phenyl)-pyridin-3-yl]-ethoxy}-naphthalen-1-yl)-propionic acid In analogy to the procedures described in example 4D] and 4E], 3-(4-hydroxy-naphthalen-1-yl)-propionic acid ethyl ester [Helvetica Chimica Acta (2001), 84(8), 2198-2211] was reacted with 2-[2-methyl-6-(4-trifluoromethyl-phenyl)-pyridin-3-yl]-ethanol (example 4K]) to give 3-(4-{2-[2-methyl-6-(4-trifluoromethyl-phenyl)-pyridin-3-yl]-ethoxy}-naphthalen-1-yl)-propionic acid ethyl ester, which was subsequently saponified to yield the title compound as colorless solid.
MS: 478.1 (M−H)−.

Example 9

3-{4-[4-Cyclopropyl-2-(4-trifluoromethyl-phenyl)-pyrimidin-5-ylmethoxy]-naphthalen-1-yl}-propionic acid A] In analogy to the procedures described in example 5C] and 5D], 3-(4-hydroxy-naphthalen-1-yl)-propionic acid ethyl ester [Helvetica Chimica Acta (2001), 84(8), 2198-2211] was reacted with 5-chloromethyl-4-cyclopropyl-2-(4-trifluoromethyl-phenyl)-pyrimidine (example 9E]) to give 3-{4-[4-cyclopropyl-2-(4-trifluoromethyl-phenyl)-pyrimidin-5-ylmethoxy]-naphthalen-1-yl}-propionic acid ethyl ester, which was subsequently saponified to yield the title compound as colorless solid.
MS: 491.1 (M−H)−.

5-Chloromethyl-4-cyclopropyl-2-(4-trifluoromethyl-phenyl)-pyrimidine used in 9A] was synthesized as follows:

B] (E,Z)-2-Cyclopropanecarbonyl-3-ethoxy-acrylic acid methyl ester

A solution of 10 g (70.34 mmol) 3-cyclopropyl-3-oxo-propionic acid methyl ester, 23.4 ml (140.68 mmol) of triethyl orthoformate in 100 ml acetic anhydride was refluxed at 150° C. for 5 h. The reaction mixture was concentrated at 95° C. under reduced pressure to give 14.35 g of crude (E,Z)-2-cyclopropanecarbonyl-3-ethoxy-acrylic acid methyl ester.
MS: 199.3 (M+H)+.

C] 4-Cyclopropyl-2-(4-trifluoromethyl-phenyl)-pyrimidine-5-carboxylic acid ethyl ester To a solution of 4.74 g (18.19 mmol) 4-trifluoromethyl-benzamidine HCl in 50 ml of ethanol was added 1.818 g (18.186 mmol) of sodium tert-butoxide. After 2 min, 3.605 g of crude (E,Z)-2-cyclopropanecarbonyl-3-ethoxy-acrylic acid methyl ester was added and the reaction mixture was then stirred over night at RT. The ethanol was removed under reduced pressure, the residue taken up in ether and washed with 1N HCl and water. The ether solution was concentrated under reduced pressure and the crude product purified by chromatography over silica gel with AcOEt/heptane 1:3 to give 4.25 g of pure 4-cyclopropyl-2-(4-trifluoromethyl-phenyl)-pyrimidine-5-carboxylic acid ethyl ester.
MS: 337.1 (M+H)+

D] [4-Cyclopropyl-2-(4-trifluoromethyl-phenyl)-pyrimidin-5-yl]-methanol

Within 10 min was dropped 31.6 ml (37.9 mmol) of 1.2 M DIBALH solution in toluene to a dry ice cooled (−50° C.) solution of 4.25 g (12.64 mmol) 4-cyclopropyl-2-(4-trifluoromethyl-phenyl)-pyrimidine-5-carboxylic acid ethyl ester in 50 ml of THF. The reaction mixture was stirred 30 min at −50° C. and after letting rise the temperature to RT, for 1 h at RT. The reaction mixture was taken up in ether and washed with 1N HCl and water. The solvent was removed under reduced pressure to give 3.72 g of pure [4-cyclopropyl-2-(4-trifluoromethyl-phenyl)-pyrimidin-5-yl]-methanol.
MS: 295.1 (M+H)+.

E] 5-Chloromethyl-4-cyclopropyl-2-(4-trifluoromethyl-phenyl)-pyrimidine

A mixture of 1.9 g (6.456 mmol) of [4-cyclopropyl-2-(4-trifluoromethyl-phenyl)-pyrimidin-5-yl]-methanol and 0.515 ml (7.1 mmol) thionylchloride in 20 ml dichloromethane was stirred for 1 h at RT. The reaction mixture was taken up in ether and washed with sodium bicarbonate solution and water. The ether phase was concentrated under reduced pressure to give 1.97 g of pure 5-chloromethyl-4-cyclopropyl-2-(4-trifluoromethyl-phenyl)-pyrimidine.
MS: 313.1 (M+H, 1 Cl)+.

Example 10

3-{4-[4-Cyclopropyl-2-(4-trifluoromethyl-phenyl)-pyrimidin-5-ylmethoxy]-5,6,7,8-tetrahydro-naphthalen-1-yl}-propionic acid In analogy to the procedures described in example 5C] and 5D], 3-(4-hydroxy-5,6,7,8-tetrahydro-naphthalen-1-yl)-propionic acid ethyl ester (example 5B]) was reacted with 5-chloromethyl-4-cyclopropyl-2-(4-trifluoromethyl-phenyl)-pyrimidine (example 9E]) to give 3-{4-[4-cyclopropyl- 2-(4-trifluoromethyl-phenyl)-pyrimidin-5-ylmethoxy]-5,6,7,8-tetrahydro-naphthalen-1-yl}-propionic acid ethyl ester, which was subsequently saponified to yield the title compound as colorless solid.

MS: 495 (M−H)−.

Example 11

3-{4-[5-(4-Trifluoromethyl-phenyl)-pyrimidin-2-ylmethoxy]-naphthalen-1-yl}-propionic acid A] In analogy to the procedures described in example 5C] and 5D], 3-(4-hydroxy-naphthalen-1-yl)-propionic acid ethyl ester [Helvetica Chimica Acta (2001), 84(8), 2198-2211] was reacted with 2-bromomethyl-5-(4-trifluoromethyl-phenyl)-pyrimidine (example 11C]) to give 3-{4-[5-(4-trifluoromethyl-phenyl)-pyrimidin-2-ylmethoxy]-naphthalen-1-yl}-propionic acid ethyl ester, which was subsequently saponified to yield the title compound as colorless solid.

MS: 451.1 (M−H)[31].

The necessary building block 2-bromomethyl-5-(4-trifluoromethyl-phenyl)-pyrimidine used in procedure above was prepared as follows:

B]
2-Methyl-5-(4-trifluoromethyl-phenyl)-pyrimidine

A solution of 7.95 g (75 mmol) of sodium carbonate in 15 ml of water was added to a mixture of 2.6 g (15 mmol) of 5-bromo-2-methylpyrimidine (Coll. Czech. Chem. Comm. 14 (1949), 223-235), of 4 g (21 mmol) of 4-(trifluoromethyl) benzene boronic acid and of 0.52 g (0.45 mmol) of tetrakis (triphenylphosphine)palladium in a mixture of 50 ml of 1,2-dimethoxy-ethane and of 30 ml of ethanol. The mixture was stirred at 80° C. for 2 hours, afterwards, it was concentrated by distilling off the major part of the organic solvents. Subsequently, the residue was extracted with 3 portions of tert.-butyl methyl ether. The combined organic phases were washed with water and brine, dried over anhydrous sodium sulfate and finally evaporated. The residue was chromatographed on silicagel with a mixture of dichloromethane/tert.-butyl methyl ether (9/1 vol./vol.) as eluent. 3 g of the title compound were obtained as greenish solid. MS: 239.2 (M+H)+.

C] 2-Bromomethyl-5-(4-trifluoromethyl-phenyl)-pyrimidine 0.31 g (1.3 mmol) of 2-methyl-5-(4-trifluoromethyl-phenyl)-pyrimidine, 0.255 g (1.43 mmol) of N-bromosuccinimide and 0.15 g (0.91 mmol) of 2,2'-azobis-(2-methyl-propionitril) were dissolved in 5 ml of carbon tetrachloride and the mixture was stirred at 75° C. Two portions of 0.13 g (0.73 mmol) of N-bromosuccinimide and 0.075 g (0.046 mmol) of 2,2'-azobis-(2-methyl-propionitril) were added to the reaction mixture, after 4 and 8 hours, respectively, and the heating was continued for additional 16 hours. After cooling to ambient temperature, the mixture was chromatographed on silicagel with dichloromethane as eluent. 0.145 g of the title compound were obtained as pale yellow solid. MS: 316.0 (M, 1Br)+.

Example 12

[rac]-(4-{1-[2-Methyl-6-(4-trifluoromethyl-phenyl)-pyridin-3-yl]-ethoxy}-naphthalen-1-yloxy)-acetic acid A] (4-Benzyloxy-naphthalen-1-yloxy)-acetic acid ethyl ester A mixture of 2 g (8 mmol) of 4-benzyloxy-naphthalen-1-ol [Journal of Medicinal Chemistry (1985), 28(6), 822-41, of 2.67 g (16 mmol) of ethyl bromoacetate and of 3.12 g (9.6 mmol) of cesium carbonate in 30 ml of acetonitrile was stirred at 60° C. for 3 hours. Subsequently, the reaction mixture was evaporated to dryness and the residue was partitioned between water and tert.-butyl methyl ether. The organic phase was separated, washed with water and brine, dried over anhydrous sodium sulfate and finally evaporated. 2.23 g of the title compound were obtained as white crystals after crystallization from n-heptane.

MS: 337.3 (M+H)+.

B] (4-Hydroxy-naphthalen-1-yloxy)-acetic acid ethyl ester 2.23 g (6.62 mmol) of (4-benzyloxy-naphthalen-1-yloxy)-acetic acid ethyl ester was dissolved in 20 ml of tetrahydrofuran and hydrogenated over 0.5 g of 10% of palladium on charcoal as catalyst at ambient temperature and atmospheric pressure. Filtering off the catalyst and evaporating the solvent yielded 1.2 g of the title compound as light brown solid.

MS: 245.2 (M−H)−.

C] [rac]-(4-{1-[2-Methyl-6-(4-trifluoromethyl-phenyl)-pyridin-3-yl]-ethoxy}-naphthalen-1-yloxy)-acetic acid In analogy to the procedures described in example 5C] and 5D], (4-hydroxy-naphthalen-1-yloxy)-acetic acid ethyl ester was reacted with [rac]-3-(1-chloro-ethyl)-2-methyl-6-(4-trifluoromethyl-phenyl)-pyridine (example 1L]) to give [rac]-(4-{1-[2-methyl-6-(4-trifluoromethyl-phenyl)-pyridin-3-yl]-ethoxy}-naphthalen-1-yloxy)-acetic acid ethyl ester, which was subsequently saponified to yield the title compound as light yellow solid.

MS: 480.2 (M−H)−.

Example 13

2-Methyl-2-(4-{methyl-[2-methyl-6-(4-trifluoromethyl-phenyl)-pyridin-3-ylmethyl]-amino}-5,6,7,8-tetrahydro-naphthalen-1-yloxy)-propionic acid A] 2-Methyl-2-(4-methylamino-5,6,7,8-tetrahydro-naphthalen-1-yloxy)-propionic acid ethyl ester In analogy to the procedures described in examples 1A] to 1D], 4-amino-5,6,7,8-tetrahydro-naphthalen-1-ol [Journal of Heterocyclic Chemistry (1982), 19(3), 633-7] was reacted with di-tert-butyl dicarbonate to yield (4-hydroxy-5,6,7,8-tetrahydro-naphthalen-1-yl)-carbamic acid tert-butyl ester. Subsequent reaction with ethyl bromoisobutyrate and Cs$_2$CO$_3$ in acetonitrile at 80° C. gave 2-(4-tert-butoxycarbonylamino-5,6,7,8-tetrahydro-naphthalen-1-yloxy)-2-methyl-propionic acid ethyl ester; this compound was then treated with methyliodide, sodium hydride in N,N-dimethylformamide to give 2-[4-(tert-butoxycarbonyl-methylamino)-5,6,7,8-tetrahydro-naphthalen-1-yloxy]-2-methyl-propionic acid ethyl ester and finally reacted with TFA in dichloromethane to yield the title compound as viscous brown oil.

MS: 292.3 (M+H)$^+$.

B] 2-Methyl-2-(4-{methyl-[2-methyl-6-(4-trifluoromethyl-phenyl)-pyridin-3-ylmethyl]-amino}-5,6,7,8-tetrahydro-naphthalen-1-yloxy)-propionic acid In analogy to the procedures described in example 5C] and 5D], 2-methyl-2-(4-methylamino-5,6,7,8-tetrahydro-naphthalen-1-yloxy)-propionic acid ethyl ester was reacted with 3-chloromethyl-2-methyl-6-(4-trifluoromethyl-phenyl)-pyridine (example 4G]) to give 2-methyl-2-(4-{methyl-[2-methyl-6-(4-trifluoromethyl-phenyl)-pyridin-3-ylmethyl]-amino}-5,6,7,8-tetrahydro-naphthalen-1-yloxy)-propionic acid ethyl ester, which was subsequently saponified to yield the title compound as colorless solid.

MS: 511.3 (M–H)$^-$.

Example 14

2-Methyl-2-(3-{2-[2-methyl-6-(4-trifluoromethyl-phenyl)-pyridin-3-yl]-ethoxy}-naphthalen-1-yloxy)-propionic acid A] In analogy to the procedures described in example 4D] and 4E], 2-(3-hydroxy-naphthalen-1-yloxy)-2-methyl-propionic acid ethyl ester (example 14C]) was reacted with 2-[2-methyl-6-(4-trifluoromethyl-phenyl)-pyridin-3-yl]-ethanol (example 4K]) to give 2-methyl-2-(3-{2-[2-methyl-6-(4-trifluoromethyl-phenyl)-pyridin-3-yl]-ethoxy}-naphthalen-1-yloxy)-propionic acid ethyl ester, which was subsequently saponified to yield the title compound as light yellow solid.

MS: 508.3 (M–H)$^-$.

2-(3-Hydroxy-naphthalen-1-yloxy)-2-methyl-propionic acid ethyl ester used in procedure 14A] has been prepared as follows:

B] 2-(3-Methoxycarbonyloxy-naphthalen-1-yloxy)-2-methyl-propionic acid ethyl ester 2.65 g (12.1 mmol) of carbonic acid 4-hydroxy-naphthalen-2-yl ester methyl ester [Journal of Agricultural and Food Chemistry (1994), 42(12), 2970-2] was dissolved in 100 ml N,N-dimethylformamide; then, 4.93 g (15.1 mmol) of cesium carbonate was added and the reaction mixture was cooled down to 2° C. 2.12 ml=2.79 g (13.9 mmol) of ethyl-bromoisobutyrate was added drop by drop and the reaction mixture was stirred for 48 hours at ambient temperature. It was subsequently partitioned between cold water and ether and extracted twice with ether; the organic phases were washed with water, dried (MgSO$_4$) and evaporated. The crude product was purified by flash chromatography (SiO$_2$, gradient of heptane/MeCl$_2$) to finally give 1.44 g of the title compound as colorless oil.

MS: 332.1 (M)$^+$.

C] 2-(3-Hydroxy-naphthalen-1-yloxy)-2-methyl-propionic acid ethyl ester 1.35 g (4.1 mmol) of 2-(3-methoxycarbonyloxy-naphthalen-1-yloxy)-2-methyl-propionic acid ethyl ester was dissolved in 30 ml of EtOH and cooled down to 5° C.; while stirring, 1.66 ml=1.45 g (4.5 mmol) of a solution of sodium ethoxide (21% in EtOH) was added and the reaction mixture then warmed up to ambient temperature. After 1 hour, it was poured into crashed ice/MeCl$_2$, the pH was adjusted to 5-6 with AcOH (1N) and the reaction mixture was subsequently extracted twice with MeCl$_2$; the organic phases were washed with water, dried (MgSO$_4$) and evaporated. The crude product was purified by flash chromatography (SiO$_2$, gradient of MeCl$_2$/MeOH) to finally give 0.95 g of the title compound as light brown oil.

MS: 273.2 (M–H)$^-$.

Example 15

2-Methyl-2-{3-[2-methyl-6-(4-trifluoromethyl-phenyl)-pyridin-3-ylmethoxy]-naphthalen-1-yloxy}-propionic acid In analogy to the procedures described in example 4D] and 4E], 2-(3-hydroxy-naphthalen-1-yloxy)-2-methyl-propionic acid ethyl ester (example 14C]) was reacted with [2-methyl-6-(4-trifluoromethyl-phenyl)-pyridin-3-yl]-methanol (example 1I]) to give 2-methyl-2-{3-[2-methyl-6-(4-trifluoromethyl-phenyl)-pyridin-3-ylmethoxy]-naphthalen-1-yloxy}-propionic acid ethyl ester, which was subsequently saponified to yield the title compound as light yellow solid.

MS: 494.2 (M–H)$^-$.

Example 16

2-(3-{2-[4-Cyclopropyl-2-(4-trifluoromethyl-phenyl)-pyrimidin-5-yl]-ethoxy}-naphthalen-1-yloxy)-2-methyl-propionic acid A] In analogy to the procedures described in example 4D] and 4E], 2-(3-hydroxy-naphthalen-1-yloxy)-2-methyl-propionic acid ethyl ester (example 14C]) was reacted with 2-[4-cyclopropyl-2-(4-trifluoromethyl-phenyl)-pyrimidin-5-yl]-ethanol (example 16B]) to give 2-(3-{2-[4-cyclopropyl-2-(4-trifluoromethyl-phenyl)-pyrimidin-5-yl]-ethoxy}-naphthalen-1-yloxy)-2-methyl-propionic acid ethyl ester, which was subsequently saponified to yield the title compound as light yellow solid.

MS: 535.3 (M–H)$^-$.

2-[4-Cyclopropyl-2-(4-trifluoromethyl-phenyl)-pyrimidin-5-yl]-ethanol used in procedure 16A] has been prepared as follows:

B] 2-[4-Cyclopropyl-2-(4-trifluoromethyl-phenyl)-pyrimidin-5-yl]-ethanol 0.60 g (1.78 mmol) of [4-cyclopropyl-2-(4-trifluoromethyl-phenyl)-pyrimidin-5-yl]-acetic acid methyl ester (prepared from 5-chloromethyl-4-cyclopropyl-2-(4-trifluoromethyl-phenyl)-pyrimidine (example 9E]) in analogy to the sequences described in examples 4H] to 4J]) was dissolved in 10 ml of abs. THF and cooled down to 0° C. It was then reacted with 3.18 nml of DIBAL-H-solution (1.2 M in toluene) and the mixture stirred for 2 h at room temperature. Careful quenching with ice/THF/H$_2$O, twofold extraction with AcOEt, washing with diluted HCl solution and brine, drying over sodium sulfate, and evaporation of the solvents left a crude product which was purified by crystallization from dichloromethane/n-heptane to deliver finally 0.53 g of the title compound as light yellow solid.

MS: 309.2 (M+H)$^+$.

Example 17

2-{4-[4-Cyclopropyl-2-(4-trifluoromethyl-phenyl)-pyrimidin-5-ylmethoxy]-naphthalen-2-yloxy}-2-methyl-propionic acid

A] In analogy to the procedures described in example 4D] and 4E], 2-(4-hydroxy-naphthalen-2-yloxy)-2-methyl-propionic acid ethyl ester (example 17D]) was reacted with [4-cyclopropyl-2-(4-trifluoromethyl-phenyl)-pyrimidin-5-yl]-methanol (example 9D]) to give 2-{4-[4-cyclopropyl-2-(4-trifluoromethyl-phenyl)-pyrimidin-5-ylmethoxy]-naphthalen-2-yloxy}-2-methyl-propionic acid ethyl ester, which was subsequently saponified to yield the title compound as yellow solid.

MS: 521.2 (M−H)⁻.

2-(4-Hydroxy-naphthalen-2-yloxy)-2-methyl-propionic acid ethyl ester used in procedure 17A] has been prepared as follows:

B] Carbonic acid Methyl ester 4-(2-trimethylsilanyl-ethoxymethoxy)-naphthalen-2-yl ester 4.62 g (21.2 mmol) of carbonic acid 4-hydroxy-naphthalen-2-yl ester methyl ester [Journal of Agricultural and Food Chemistry (1994), 42(12), 2970-2] was dissolved in 150 ml of MeCl$_2$, 4.95 ml=4.71 g (25.4 mmol) of 2-(trimethylsilyl)-ethoxymethylchloride was added and this mixture cooled down to 2° C. 11.1 ml=8.38 g (63.5 mmol) of N-ethyl-diisoproylamine was added drop by drop and then, reaction was warmed up to ambient temperature. After 48 hours, it was poured into crashed ice and extracted twice with MeCl$_2$; the organic phases were washed with water, dried (MgSO$_4$) and evaporated. The crude product was purified by flash chromatography (SiO$_2$, gradient of n-heptane/MeCl$_2$) to give 5.57 g of carbonic acid methyl ester 4-(2-trimethylsilanyl-ethoxymethoxy)-naphthalen-2-yl ester as colorless oil.

MS: 348.1 (M)⁺.

C] 4-(2-Trimethylsilanyl-ethoxymethoxy)-naphthalen-2-ol 5.82 g (16.7 mmol) of carbonic acid methyl ester 4-(2-trimethylsilanyl-ethoxymethoxy)-naphthalen-2-yl ester was dissolved in 100 ml of methanol and cooled down to 5° C.; 3.4 ml=3.30 g (18.4 mmol) of sodium methoxide (5.4 molar in MeOH) was added and the reaction mixture then warmed up to room temperature. After one hour, it was poured into crashed ice, the pH was adjusted to 5-6 with AcOH (1N) and the reaction mixture subsequently extracted twice with MeCl$_2$; the organic phases were washed with water, dried (MgSO$_4$) and evaporated. The crude product was purified by flash chromatography (SiO$_2$, gradient of n-heptane/MeCl$_2$) to give 4.23 g of 4-(2-trimethylsilanyl-ethoxymethoxy)-naphthalen-2-ol as light brown oil.

MS: 289.1 (M−H)⁻.

D] 2-(4-Hydroxy-naphthalen-2-yloxy)-2-methyl-propionic acid ethyl ester 1.58 g (3.90 mmol) of 2-methyl-2-[4-(2-trimethylsilanyl-ethoxymethoxy)-naphthalen-2-yloxy]-propionic acid ethyl ester (prepared from 4-(2-trimethylsilanyl-ethoxymethoxy)-naphthalen-2-ol, ethyl bromoisobutyrate, cesium carbonate, in analogy to the procedure described in example 14B] was dissolved in 20 ml of EtOH; then, 1.95 ml of HCl/EtOH-solution (6 molar) was added drop by drop. After 7 hours stirring at room temperature, the solvent was removed by evaporation and the residue was partitioned between water and MeCl$_2$. The organic phase was separated, washed with water, dried (MgSO$_4$) and evaporated. The crude product was purified by chromatography over silica gel with a gradient of AcOEt/heptane to give 1.06 g of pure 2-(4-hydroxy-naphthalen-2-yloxy)-2-methyl-propionic acid ethyl ester as light brown oil.

MS: 275.1 (M+H)⁺.

Example 18

2-(4-{2-[4-Cyclopropyl-2-(4-trifluoromethyl-phenyl)-pyrimidin-5-yl]-ethoxy}-naphthalen-2-yloxy)-2-methyl-propionic acid

In analogy to the procedures described in example 4D] and 4E], 2-(4-hydroxy-naphthalen-2-yloxy)-2-methyl-propionic acid ethyl ester (example 17D]) was reacted with 2-[4-cyclopropyl-2-(4-trifluoromethyl-phenyl)-pyrimidin-5-yl]-ethanol (example 16B]) to give 2-(4-{2-[4-cyclopropyl-2-(4-trifluoromethyl-phenyl)-pyrimidin-5-yl]-ethoxy}-naphthalen-2-yloxy)-2-methyl-propionic acid ethyl ester, which was subsequently saponified to yield the title compound as light yellow solid.

MS: 535.3 (M−H)⁻.

Example 19

2-Methyl-2-(4-{2-[2-methyl-6-(4-trifluoromethyl-phenyl)-pyridin-3-yl]-ethoxy}-naphthalen-2-yloxy)-propionic acid

In analogy to the procedures described in example 4D] and 4E], 2-(4-hydroxy-naphthalen-2-yloxy)-2-methyl-propionic acid ethyl ester (example 17D]) was reacted with 2-[2-methyl-6-(4-trifluoromethyl-phenyl)-pyridin-3-yl]-ethanol (example 4K]) to give 2-methyl-2-(4-{2-[2-methyl-6-(4-trifluoromethyl-phenyl)-pyridin-3-yl]-ethoxy}-naphthalen-2-yloxy)-propionic acid ethyl ester, which was subsequently saponified to yield the title compound as orange solid.

MS: 508.3 (M−H)⁻.

Example 20

2-Methyl-2-{4-[2-methyl-6-(4-trifluoromethyl-phenyl)-pyridin-3-ylmethoxy]-naphthalen-2-yloxy}-propionic acid

In analogy to the procedures described in example 4D] and 4E], 2-(4-hydroxy-naphthalen-2-yloxy)-2-methyl-propionic acid ethyl ester (example 17D]) was reacted with [2-methyl-6-(4-trifluoromethyl-phenyl)-pyridin-3-yl]-methanol (example 1I]) to give 2-methyl-2-{4-[2-methyl-6-(4-trifluoromethyl-phenyl)-pyridin-3-ylmethoxy]-naphthalen-2-yloxy}-propionic acid ethyl ester, which was subsequently saponified to yield the title compound as yellow solid.

MS: 494.2 (M−H)⁻.

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcristalline cellulose and the mixture is granulated with a solution of polyvinylpyrrolidon in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Gelatine | 150.0 mg |
| Phenol | 4.7 mg |
| Sodium carbonate | to obtain a final pH of 7 |
| Water for injection solutions | ad 1.0 ml |

Example D

Soft gelatin capsules containing the following ingredients can be manufactured in a conventional manner:

| | |
|---|---|
| Capsule contents | |
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula (I) | 50.0 mg |
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K 30 | 10.0 mg |
| Magnesiumstearate | 10.0 mg |
| Flavoring additives | 1.0 mg |

The active ingredient is mixed with lactose, microcristalline cellulose and sodium carboxymethyl cellulose and granulated with a mixture of polyvinylpyrrolidon in water. The granulate is mixed with magnesiumstearate and the flavouring additives and filled into sachets.

What is claimed is:
1. A Compound of the formula

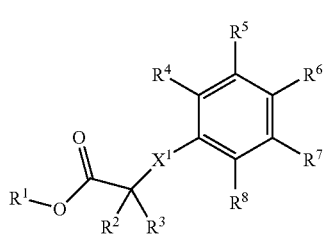

I and enantiomers and pharmaceutically acceptable salts and esters thereof, wherein
$X^1$ is O or $CH_2$;
$R^1$ is hydrogen or $C_{1-7}$-alkyl;
$R^2$ is hydrogen or $C_{1-7}$-alkyl,
or, if $X^1$ is $CH_2$, $R^2$ is hydrogen, $C_{1-7}$-alkyl or $C_{1-7}$-alkoxy;
$R^3$ is hydrogen or $C_{1-7}$-alkyl;
$R^4$ and $R^5$ or $R^5$ and $R^6$ are bonded to each other to form a ring together with the carbon atoms to which they are attached, and $R^4$ and $R^5$ or $R^5$ and $R^6$ together are:

—CH=CH—CH=CH— or
—(CH$_2$)$_p$,
wherein p is 4; and
R$^4$ and R$^6$ are engaged in a ring structure as defined above or independently from each other are selected from the group consisting of hydrogen, C$_{1-7}$-alkyl, C$_{3-7}$-cycloalkyl, halogen, C$_{1-7}$-alkoxy-C$_{1-7}$-alkyl, C$_{2-7}$-alkenyl, C$_{2-7}$-alkinyl, fluoro-C$_{1-7}$-alkyl, cyano-C$_{1-7}$-alkyl or cyano;
R$^7$ and R$^8$ independently from each other are selected from the group consisting of hydrogen, C$_{1-7}$-alkyl, C$_{3-7}$-cycloalkyl, halogen, C$_{1-7}$-alkoxy-C$_{1-7}$-alkyl, C$_{2-7}$-alkenyl, C$_{2-7}$-alkinyl, fluoro-C$_{1-7}$-alkyl, cyano-C$_{1-7}$-alkyl or cyano;
and one of R$^6$ and R$^7$ is

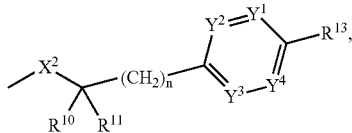

wherein
X$^2$ is O or NR$^9$;
R$^9$ is hydrogen, C$_{1-7}$-alkyl, C$_{3-7}$-cycloalkyl, fluoro-C$_{1-7}$-alkyl, hydroxy-C$_{2-7}$-alkyl, or C$_{1-7}$-alkoxy-C$_{2-7}$-alkyl;
Y$^1$ is N and Y$^2$, Y$^3$ and Y$^4$ are C—R$^{12}$ or Y$^1$ and Y$^4$ are N and Y$^2$ and Y$^3$ are C—R$^{12}$;
R$^{10}$ is hydrogen, C$_{1-7}$-alkyl, C$_{3-7}$-cycloalkyl, or fluoro-C$_{1-7}$-alkyl;
R$^{11}$ is hydrogen, C$_{1-7}$-alkyl, or C$_{1-7}$-alkoxy-C$_{1-7}$-alkyl;
R$^{12}$ independently from each other in each occurrence is selected from the group consisting of hydrogen, C$_{1-7}$-alkyl and C$_{3-7}$-cycloalkyl;
R$^{13}$ is aryl or heteroaryl; and
n is 0, 1 or 2;
provided that compounds of formula I are excluded, wherein
X$^1$ is O, R$^2$ and R$^3$ are hydrogen,
R$^6$ is equal to

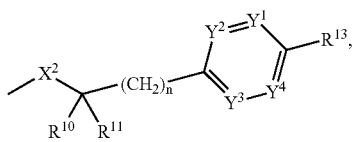

X$^2$ is O and R$^{10}$ and R$^{11}$ are hydrogen.

2. The Compound of claim 1, wherein R$^1$ is hydrogen.

3. The Compound of claim 2, wherein X$^2$ is —NR$^9$ and R$^9$ is selected from the group consisting of hydrogen, C$_{1-7}$-alkyl, C$_{3-7}$-cycloalkyl, fluoro-C$_{1-7}$-alkyl, hydroxy-C$_{2-7}$-alkyl, or C$_{1-7}$-alkoxy-C$_{2-7}$-alkyl.

4. The Compound of claim 3, wherein R$^9$ is C$_{1-7}$-alkyl.

5. The Compound of claim 4, wherein said compound is selected from the group consisting of
[4-(methyl-{1-[2-methyl-6-(4-trifluoromethyl-phenyl)-pyridin-3-yl]-ethyl}-amino)-naphthalen-1-yloxy]-acetic acid;
[4-(methyl-{1-[2-methyl-6-(3-trifluoromethyl-phenyl)-pyridin-3-yl]-propyl}-amino)-naphthalen-1-yloxy]-acetic acid; and
[4-(methyl-{1-[2-methyl-6-(3-trifluoromethyl-phenyl)-pyridin-3-yl]-butyl}-amino)-naphthalen-1-yloxy]-acetic acid.

6. The compound of claim 4, wherein said compound is 2-methyl-2-(4-{methyl-[2-methyl-6-(4-trifluoromethyl-phenyl)-pyridin-3-ylmethyl]-amino}-5,6,7,8-tetrahydro-naphthalen-1-yloxy)-propionic acid.

7. The Compound of claim 1, wherein X$^1$ is CH$_2$.

8. The Compound of claim 7, wherein said compound is selected from the group consisting of
2-methoxy-3-(4-{2-[2-methyl-6-(4-trifluoromethyl-phenyl)-pyridin-3-yl]-ethoxy}-naphthalen-2-yl)-propionic acid;
3-{4-[2-methyl-6-(4-trifluoromethyl-phenyl)-pyridin-3-ylmethoxy]-5,6,7,8-tetrahydro-naphthalen-1-yl}-propionic acid; and
3-{4-[2-methyl-6-(4-trifluoromethyl-phenyl)-pyridin-3-ylmethoxy]-naphthalen-1-yl}-propionic acid.

9. The Compound of claim 7, wherein said compound is selected from the group consisting of
3-(4-{2-[2-methyl-6-(4-trifluoromethyl-phenyl)-pyridin-3-yl]-ethoxy}-5,6,7,8-tetrahydro-naphthalen-1-yl)-propionic acid,
3-(4-{2-[2-methyl-6-(4-trifluoromethyl-phenyl)-pyridin-3-yl]-ethoxy}-naphthalen-1-yl)-propionic acid,
3-{4-[4-cyclopropyl-2-(4-trifluoromethyl-phenyl)-pyrimidin-5-ylmethoxy]-naphthalen-1-yl}-propionic acid,
3-{4-[4-cyclopropyl-2-(4-trifluoromethyl-phenyl)-pyrimidin-5-ylmethoxy]-5,6,7,8-tetrahydro-naphthalen-1-yl}-propionic acid, and
3-{4-[5-(4-trifluoromethyl-phenyl)-pyrimidin-2-ylmethoxy]-naphthalen-1-yl}-propionic acid.

10. The Compound of claim 1, wherein R$^{10}$ is C$_{1-7}$-alkyl.

11. The compound of claim 10, wherein said compound is (4-{1-[2-methyl-6-(4-trifluoromethyl-phenyl)-pyridin-3-yl]-ethoxy}-naphthalen-1-yloxy)-acetic acid.

12. The Compound of claim 1, wherein R$^2$ is C$_{1-7}$-alkyl.

13. The Compound of claim 12, wherein R$^3$ is C$_{1-7}$-alkyl.

14. The Compound of claim 1, wherein X$^1$ is O and R$^2$ and R$^3$ are C$_{1-7}$-alkyl.

15. The Compound of claim 14, wherein said compound is selected from the group consisting of
2-methyl-2-(3-{2-[2-methyl-6-(4-trifluoromethyl-phenyl)-pyridin-3-yl]-ethoxy}-naphthalen-1-yloxy)-propionic acid,
2-methyl-2-{3-[2-methyl-6-(4-trifluoromethyl-phenyl)-pyridin-3-ylmethoxy]-naphthalen-1-yloxy}-propionic acid,
2-(3-{2-[4-cyclopropyl-2-(4-trifluoromethyl-phenyl)-pyrimidin-5-yl]-ethoxy}-naphthalen-1-yloxy)-2-methyl-propionic acid,
2-{4-[4-cyclopropyl-2-(4-trifluoromethyl-phenyl)-pyrimidin-5-ylmethoxy]-naphthalen-2-yloxy}-2-methyl-propionic acid,
2-(4-{2-[4-cyclopropyl-2-(4-trifluoromethyl-phenyl)-pyrimidin-5-yl]-ethoxy}-naphthalen-2-yloxy)-2-methyl-propionic acid,
2-methyl-2-(4-{2-[2-methyl-6-(4-trifluoromethyl-phenyl)-pyridin-3-yl]-ethoxy}-naphthalen-2-yloxy)-propionic acid, and
2-methyl-2-{4-[2-methyl-6-(4-trifluoromethyl-phenyl)-pyridin-3-ylmethoxy]-naphthalen-2-yloxy}-propionic acid.

16. The Compound of claim 1, wherein R$^{13}$ is unsubstituted phenyl or phenyl substituted with one to three groups selected from from C$_{1-7}$-alkyl, C$_{1-7}$-alkoxy, halogen, fluoro-C$_{1-7}$-alkyl and cyano.

17. The Compound of claim 16, wherein R$^{13}$ is phenyl substituted with halogen or fluoro-C$_{1-7}$-alkyl.

18. The Compound of claim 1 having the formula

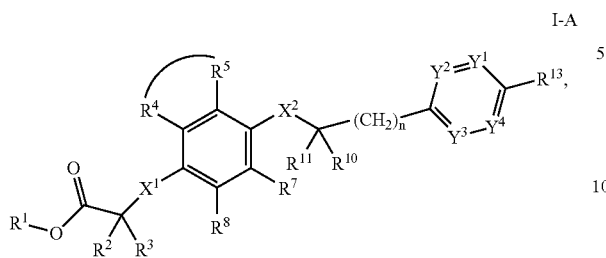

I-A wherein
R$^4$ and R$^5$ form a ring together with the carbon atoms to which they are attached, and R$^4$ and R$^5$ together are:
—CH=CH—CH=CH— or,
—(CH$_2$)$_p$—
wherein p is 4 and
X$^1$, X$^2$, Y$^1$ to Y$^4$, R$^1$, R$^2$, R$^3$, R$^7$, R$^8$, R$^{10}$, R$^{11}$, R$^{13}$ and n are as defined in claim 1;
provided that compounds of formula I-A are excluded, wherein X$^1$ is O, R$^2$ and R$^3$ are hydrogen, X$^2$ is O and R$^{10}$ and R$^{11}$ are hydrogen.

19. The Compound of claim 1 having the formula

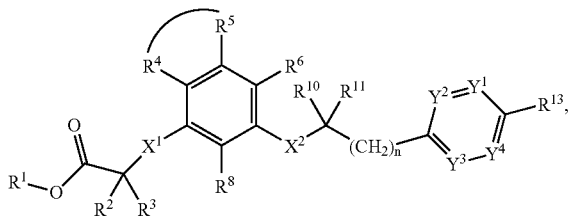

I-B wherein
R$^4$ and R$^5$ form a ring together with the carbon atoms to which they are attached, and R$^4$ and R$^5$ together are
—CH=CH—CH=CH— or
—(CH$_2$)$_p$—,
wherein p is 4 and
X$^1$, X$^2$, Y$^1$ to Y$^4$, R$^1$, R$^2$, R$^3$, R$^6$, R$^8$, R$^{10}$, R$^{11}$, R$^{13}$ and n are as defined in claim 1.

20. The Compound of claim 1 having the formula

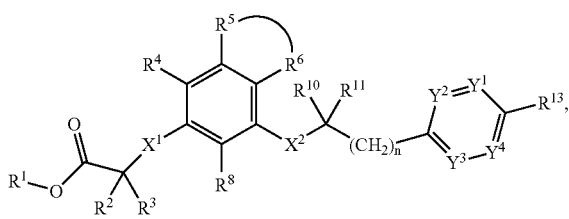

I-C wherein
R$^5$ and R$^6$ form a ring together with the carbon atoms to which they are attached, and R$^5$ and R$^6$ together are —CH=CH—CH=CH— or
—(CH$_2$)$_p$—,
wherein p is 4 and
X$^1$, X$^2$, Y$^1$ to Y$^4$, R$^1$, R$^2$, R$^3$, R$^4$, R$^8$, R$^{10}$, R$^{11}$, R$^{13}$ and n are as defined in claim 1.

21. A process for the manufacture of a compound of claim 1, which process comprises reacting a compound of formula

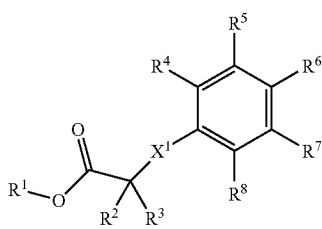

II wherein R$^1$ is C$_{1-7}$-alkyl, R$^2$ to R$^8$ are as defined in claim 1 and R$^6$ or R$^7$ are selected from —OH, —SH or —NHR$^9$, wherein R$^9$ is as in claim 1, defined,
with a compound of formula

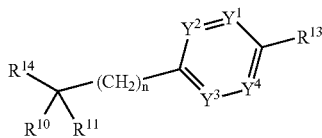

III wherein Y$^1$ to Y$^4$, R$^{10}$, R$^{11}$, R$^{13}$ and n are as defined in claim 1 and R$^{14}$ is —OH, —Cl, —Br, —I or another leaving group, to obtain a compound of formula

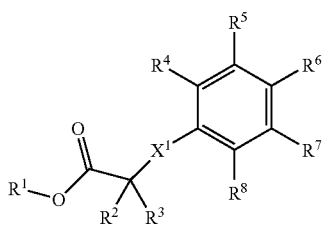

I wherein R$^6$ or R$^7$ is

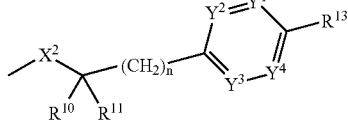

and wherein X$^2$ is O or —NR$^9$, R$^1$ is C$_{1-7}$-alkyl and X$^1$, Y$^1$ to Y$^4$, R$^2$ to R$^{13}$ and n are as defined in claim 1,
and optionally hydrolysing the ester group to obtain a compound of formula I, wherein R$^1$ is hydrogen.

22. A pharmaceutical composition which comprises a compound of the formula

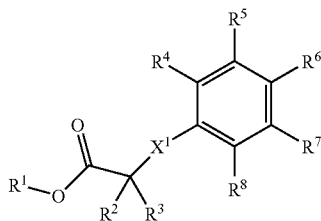

and enantiomers and pharmaceutically acceptable salts and esters thereof, wherein $X^1$ is O or $CH_2$;

$R^1$ is hydrogen or $C_{1-7}$-alkyl;

$R^2$ is hydrogen or $C_{1-7}$-alkyl,
or, if $X^1$ is $CH_2$, $R^2$ is hydrogen, $C_{1-7}$-alkyl or $C_{1-7}$-alkoxy;

$R^3$ is hydrogen or $C_{1-7}$-alkyl;

$R^4$ and $R^5$ or $R^5$ and $R^6$ are bonded to each other to form a ring together with the carbon atoms to which they are attached, and $R^4$ and $R^5$ or $R^5$ and $R^6$ are together are:

—CH=CH—CH=CH— or

—$(CH_2)_p$—, wherein p is 4; and $R^4$ and $R^6$ are engaged in a ring structure as defined above or independently from each other are selected from the group consisting of hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, cyano-$C_{1-7}$-alkyl or cyano;

$R^7$ and $R^8$ independently from each other are selected from the group consisting of hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, cyano-$C_{1-7}$-alkyl or cyano;

and one of $R^6$ and $R^7$ is

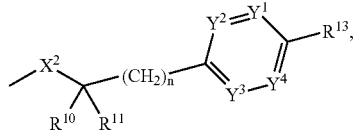

wherein $X^2$ is S, O, or $NR^9$;

$R^9$ is hydrogen, $C_{1-7}$-alkyl, $C_{3-7}$-cycloalkyl, fluoro-$C_{1-7}$-alkyl, hydroxy-$C_{2-7}$-alkyl, or $C_{1-7}$-alkoxy-$C_{2-7}$-alkyl;

$Y^1$ is N and $Y^2$, $Y^3$ and $Y^4$ are C—$R^{12}$ or $Y^1$ and $Y^4$ are N and $Y^2$ and $Y^3$ are C—$R^{12}$;

$R^{10}$ is hydrogen, $C_{1-7}$-alkyl, $C_{3-7}$-cycloalkyl, or fluoro-$C_{1-7}$-alkyl;

$R^{11}$ is hydrogen, $C_{1-7}$-alkyl, or $C_{1-7}$-alkoxy-$C_{1-7}$-alkyl;

$R^{12}$ independently from each other in each occurrence is selected from the group consisting of hydrogen, $C_{1-7}$-alkyl and $C_{3-7}$-cycloalkyl;

$R^{13}$ is aryl or heteroaryl; and n is 0, 1 or 2;

provided that compounds of formula I are excluded, wherein $X^1$ is O, $R^2$ and $R^3$ are hydrogen, $R^6$ is equal to

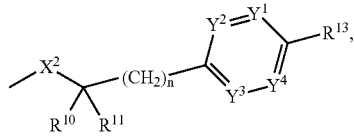

$X^2$ is O or S, and $R^{10}$ and $R^{11}$ are hydrogen together with a pharmaceutically acceptable carrier and/or adjuvant. pharmaceutically acceptable carrier and/or adjuvant.

* * * * *